United States Patent
Weber et al.

(10) Patent No.: US 10,932,768 B2
(45) Date of Patent: Mar. 2, 2021

(54) ANCHOR ARRANGEMENT AND SURGICAL INSTRUMENT FOR SETTING AN ANCHOR ARRANGEMENT

(71) Applicant: H&B ELECTRONIC GMBH & CO. KG, Deckenpfronn (DE)

(72) Inventors: Wilfried Weber, Schopfloch (DE); Wolfgang Stauss, Rangendingen (DE); Tobias Morlok, Mötzingen (DE)

(73) Assignee: H&B ELECTRONIC GMBH & CO. KG, Deckenpfronn (DE)

( * ) Notice: Subject to any disclaimer, the term of this patent is extended or adjusted under 35 U.S.C. 154(b) by 232 days.

(21) Appl. No.: 15/557,022

(22) PCT Filed: Mar. 15, 2016

(86) PCT No.: PCT/EP2016/055513
§ 371 (c)(1),
(2) Date: Sep. 8, 2017

(87) PCT Pub. No.: WO2016/146615
PCT Pub. Date: Sep. 22, 2016

(65) Prior Publication Data
US 2018/0055506 A1    Mar. 1, 2018

(30) Foreign Application Priority Data
Mar. 17, 2015   (DE) .................... 20 2015 002 244.8

(51) Int. Cl.
*A61B 17/04*      (2006.01)
*A61B 17/06*      (2006.01)
(Continued)

(52) U.S. Cl.
CPC .... *A61B 17/0401* (2013.01); *A61B 17/06166* (2013.01); *A61B 17/0467* (2013.01);
(Continued)

(58) Field of Classification Search
CPC ........ A61B 17/0401; A61B 2017/0409; A61B 2017/0414; A61B 17/06166; A61B 2017/0646
See application file for complete search history.

(56) References Cited

U.S. PATENT DOCUMENTS 5,041,129 A * 8/1991 Hayhurst ........... A61B 17/0401
606/139
5,647,874 A * 7/1997 Hayhurst ........... A61B 17/0401
606/232
(Continued)

FOREIGN PATENT DOCUMENTS

| EP | 1 408 848 B1 | 6/2010 |
| KR | 10-2006-0009698 A | 2/2006 |
| WO | WO 95/11631 A1 | 5/1995 |

OTHER PUBLICATIONS

International Search Report (PCT/ISA/210) issued in PCT/EP2016/055513, dated Jun. 22, 2016.

*Primary Examiner* — Sarah A Simpson
(74) *Attorney, Agent, or Firm* — Birch, Stewart, Kolasch & Birch, LLP

(57) ABSTRACT

An anchor arrangement is provided for surgical tissue repair, such as in particular for repair of a meniscus tear, having at least one first anchor and one second anchor, which are movable along a hollow needle for placement on a tissue to be repaired and connected to each other via a seam element. The first anchor and the second anchor each extend between a distal end and a proximal end and form a guide surface on the outside thereof for contacting an inside of a hollow needle at least in part. In addition, there are deflectors on the anchors, via which a torque can be applied at least in part to the anchors during or after setting. At least one of the anchors has at least two anchor sections, which are movable relative to each other and which can be pivoted relative to (Continued)

Figure 1:
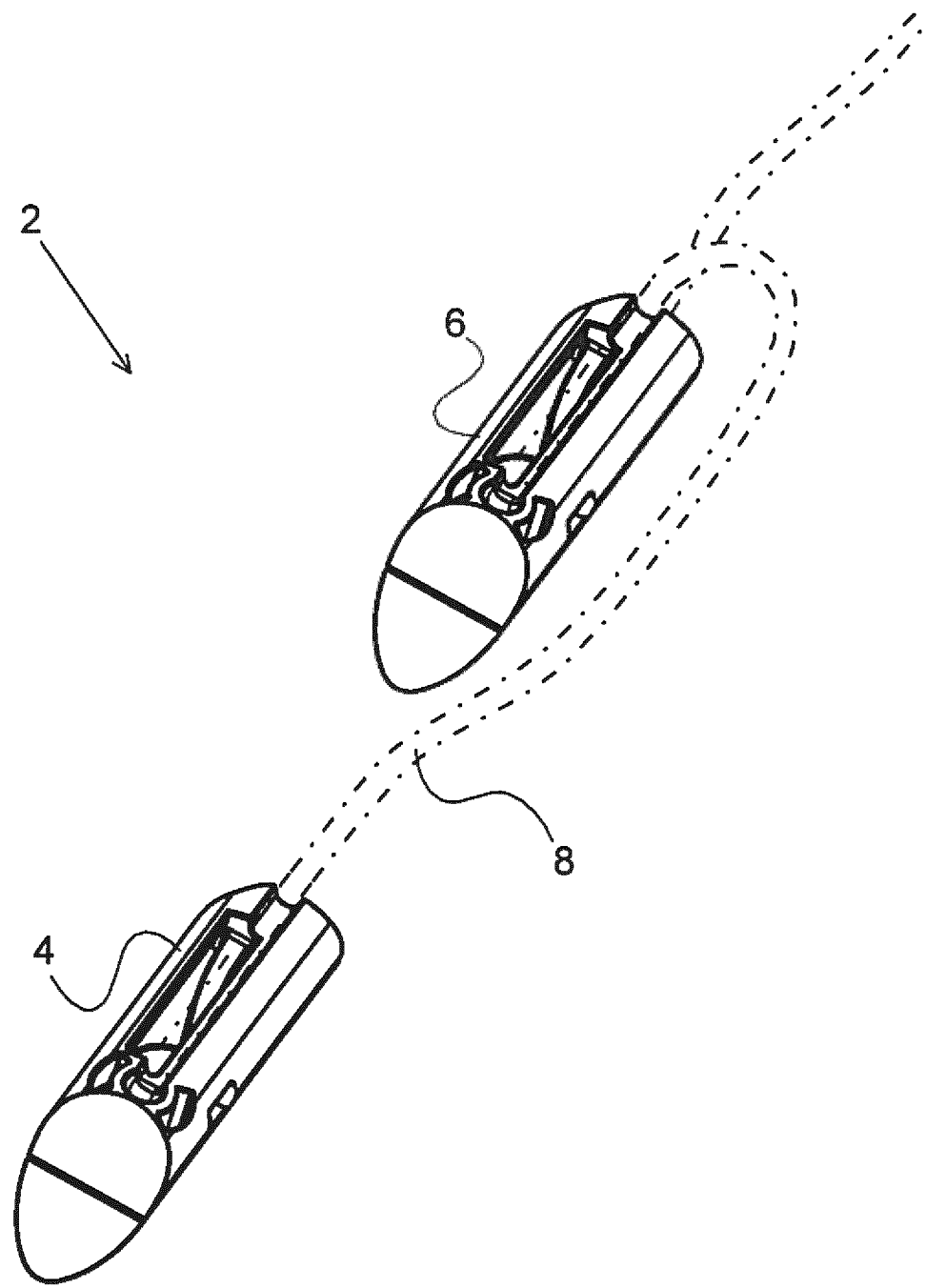

each other between a folded position, in which the guide surface spans a cross-section deviating from a circular profile, and an unfolded position.

19 Claims, 30 Drawing Sheets

(51) Int. Cl.
  *A61B 17/00* (2006.01)
  *A61B 17/064* (2006.01)
  *A61F 2/08* (2006.01)

(52) U.S. Cl.
  CPC ............ *A61B 2017/00004* (2013.01); *A61B 2017/0053* (2013.01); *A61B 2017/00477* (2013.01); *A61B 2017/00867* (2013.01); *A61B 2017/00876* (2013.01); *A61B 2017/042* (2013.01); *A61B 2017/0409* (2013.01); *A61B 2017/0414* (2013.01); *A61B 2017/0417* (2013.01); *A61B 2017/0422* (2013.01); *A61B 2017/0435* (2013.01); *A61B 2017/0464* (2013.01); *A61B 2017/061* (2013.01); *A61B 2017/0619* (2013.01); *A61B 2017/0646* (2013.01); *A61F 2/0811* (2013.01)

(56) References Cited

U.S. PATENT DOCUMENTS

| | | | |
|---|---|---|---|
| 6,102,934 A | | 8/2000 | Li |
| 6,146,406 A | * | 11/2000 | Shluzas ............ A61B 17/0401 606/232 |
| 2003/0135239 A1 | | 7/2003 | Gabriel et al. |
| 2006/0190042 A1 | | 8/2006 | Stone et al. |
| 2007/0276412 A1 | | 11/2007 | Catanese, III et al. |
| 2011/0071549 A1 | | 3/2011 | Caborn et al. |
| 2011/0092988 A1 | * | 4/2011 | Cohen ................ A61B 17/0057 606/142 |
| 2012/0157761 A1 | | 6/2012 | Crank et al. |
| 2013/0345751 A1 | | 12/2013 | Beck |
| 2015/0250470 A1 | * | 9/2015 | Vargas ............... A61B 17/0401 606/232 |

* cited by examiner

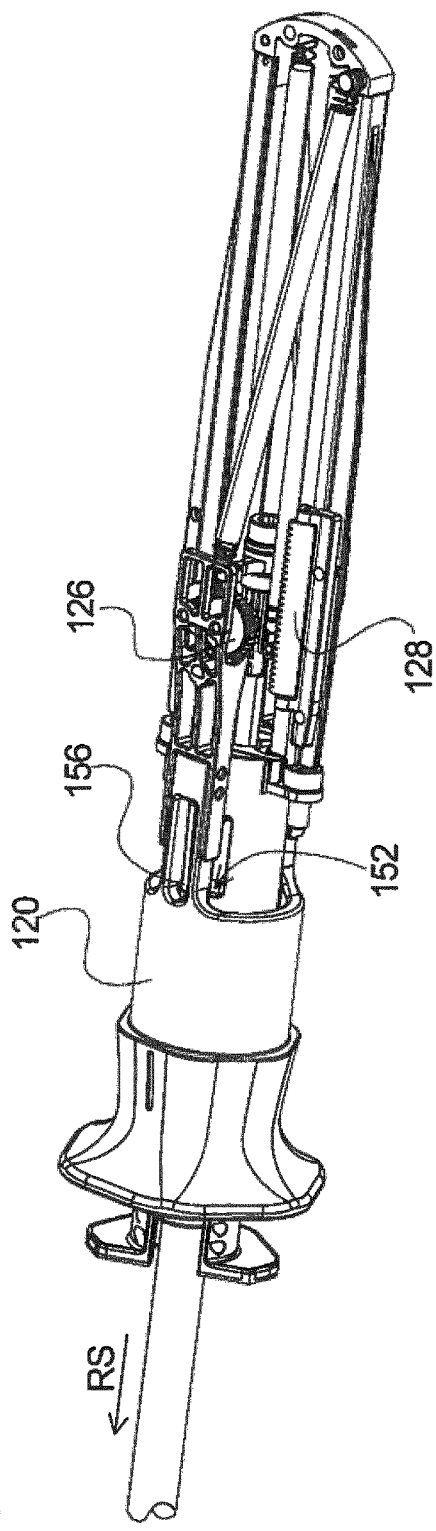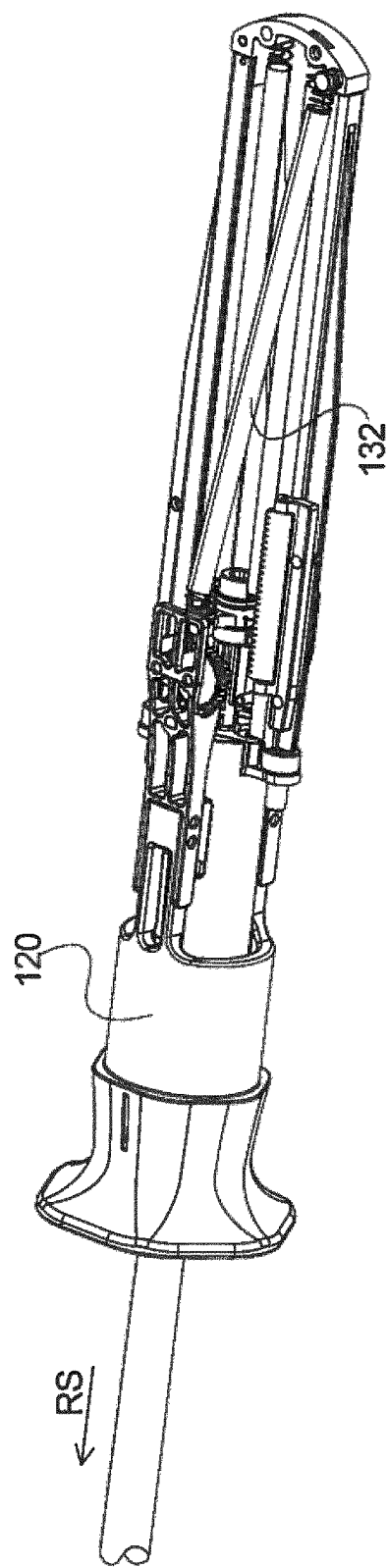

ANCHOR ARRANGEMENT AND SURGICAL INSTRUMENT FOR SETTING AN ANCHOR ARRANGEMENT

The invention relates to an anchor arrangement for surgical tissue repair, in particular for repair of a meniscus tear, according to the preamble of claim 1. The invention further relates to a surgical instrument for setting an anchor arrangement. The anchor arrangement comprises at least a first anchor and a second anchor, which are movable along a hollow needle for placement on a tissue to be repaired and can be ejected from said hollow needle. The at least two anchors are connected together by means of a suture element. In order to repair the tissue concerned, at least one part of the suture element connecting the two anchors can be shortened, by which means for example a tear of the tissue can be closed. The first anchor and the second anchor extend in each case between a distal end and a proximal end, and have a guide surface on the outside thereof, which serves to guide the needle along an inside of the hollow needle. There are deflection means on the anchors, via which a torque can be applied at least in part to the anchors, during or after setting. It is therefore possible by means of the provided deflection means, to apply a torque to the anchor while still inside the hollow needle or alternatively after exit from the needle tip, in order to move the entire anchor or parts thereof in a direction deviating from the setting direction. As a result, the anchors can be moved at least partially in the transverse direction to the hollow needle or to a passage in the tissue created by means of the hollow needle. This transverse orientation, existing at least in some regions, can prevent the anchors from being pulled back through the passage when tension is applied to the suture element.

An anchor arrangement and a setting device for fastening tissue to a bone, without the need to introduce a hole into the bone beforehand, are known from US 2013/0345751 A1. To this end, the anchor arrangement comprises a plurality of anchors having a cylindrical outer surface that can be ejected from the setting device. Into each of these is introduced a drilled hole arranged offset relative to a longitudinal axis for attaching a cord-like suture element and an oblique section formed by a material recess. After the setting, a torque can thus be applied to the anchors by pulling on the suture element, by means of which they can tilt in a bore hole created by the setting device.

An anchor arrangement is known from EP 1 408 848 B1, in which a surgical instrument can be set by means of a hollow needle. In order to set the anchor in a specified orientation, the hollow needle comprises a longitudinal slot opening into the needle tip. A fin is guided along this slot, which protrudes respectively from a base body. In addition recesses are introduced into the fins, on which a suture element connecting the anchors is attached.

A disadvantage of the known anchor arrangement is that during penetration of the tissue to be repaired, said tissue must be partially displaced by the fin protruding from the hollow needle. In addition, during penetration of the tissue, tissue particles can be picked up at the needle tip and at the slot and separated from the rest of the tissue, which are therefore no longer available for the subsequent healing of the tissue material. In addition, during setting of such anchor arrangements by means of a hollow needle, it is often the case that after penetrating the tissue and being set out of the hollow needle, on pulling on the suture element, the anchor can be pulled out of the tissue again through the point of penetration.

The problem addressed by the present invention is that of avoiding the above stated disadvantages for an anchor arrangement of the type in question, and ensuring an accurate setting and a minimised stress on the tissue concerned.

The stated problem is solved by an anchor arrangement comprising the features of claim 1. In this case, at least one of the anchors comprises at least two anchor sections that can be deflected or pivoted relative to one another, wherein, in a folded position of the anchor sections, a part of the guide surface that can contact the inside of the hollow needle, generates or forms a cross-section that deviates at least in sections from a circular profile. The parts of the anchor which form the guide surface thereof in the folded position, thus generate a virtual contour perpendicular to the setting direction, that deviates from a cylindrical shape. This allows the respective anchor to be guided accurately in the folded position thereof with respect to a linear axis of the hollow needle, in a specified rotational position with respect to the correspondingly-shaped hollow needle, without the need for further guide elements. In this way, the anchor can have a relatively compact form and the hollow needle can be designed to be relatively thin, resulting in reduced stress of the tissue to be repaired. Through the fact that the anchor sections can be pivoted with respect to one another, the anchor can be adjusted between the particularly compact shape in the folded position, in which it can be moved along a relatively thin hollow needle, and a widened shape in the unfolded position, in which the pivoting anchor sections prevent re-entry into a passage through the tissue concerned. This folding function ensures that after a setting procedure, by pulling on the suture element, the anchor can no longer be pulled back through the previously produced puncture opening in the tissue.

The at least two anchor sections are connected together via a joint. The joint allows a particularly easy deflecting or unfolding of the anchor sections concerned. This enables the application of a very small torque to bring the anchor into the unfolded position. Alternatively, or in addition, at least two anchor sections are formed as a single piece and connected to one another by an integral hinge. This allows the relevant anchor sections of the anchor to be produced together in one piece. This enables both lower production costs as well as a relatively stable overall design of the anchor.

In a particularly advantageous embodiment, in the folded position of the anchor sections which are moveable relative to one another, the guide surface forms a heart-shape, oval or egg-shape, in the sense of a circumferentially convex or strongly convex profile. Through such a profile of the guide surface or through such an outer contour of the anchor which is generated on the guide surface in the folded position, a very compact shape is achieved despite the non-rotatable guidance thereof along a correspondingly formed needle, which allows a particularly accurate setting that is at the same time gentle on the tissue.

It is also particularly advantageous if the at least two anchor sections are pretensioned towards the unfolded position, so that during setting or directly after exit from the hollow needle, the anchor can automatically be brought into the unfolded position. In addition, the anchor sections can comprise an opening through which the suture element is respectively guided. In this way, the suture element can be used to pivot the anchor sections. The suture element can also be used to protect against loss of the individual anchor sections. Thus it is advantageous if the suture element is deflected on at least two anchor sections, in such a way that an unfolding torque can be applied to said anchor sections via the suture element. In this way, the point in time when the anchor is brought into the fully unfolded position is determined by the person setting the anchor arrangement, by applying a tensile force on the suture element.

In a further advantageous embodiment, each of the two anchor sections is supported in the unfolded position by a respective end stop of the other anchor section, which enables a particularly stable end position in the unfolded position. It is also advantageous if the at least two anchor sections can lock or latch in the unfolded position, by means of which an undesired partial or complete return or re-deformation of the anchor into the folded position is prevented, such as for example by the positioning of the anchor on the tissue to be repaired.

It is thus advantageous if at least one of the anchors has a rough surface for contacting the tissue material to be repaired. After setting, this rough surface ensures an additional position stability of the anchor in contact with the tissue. It is also an advantage if the at least two anchor sections form a concave contact surface for attachment to the tissue, in the unfolded position. This allows the anchor to also be brought into contact with a convex surface of the tissue to be repaired, as may be present for example during the repair of a meniscus, at least over a large part of the length thereof. Furthermore, it is advantageous if the at least two anchor sections each have a rounding at a respective free end. The rounding can avoid the free end of the anchor sections becoming attached to the tissue concerned before attaining the unfolded position.

In a further advantageous embodiment, in the folded position, the at least two anchor sections form a common spreading receptacle at the proximal end of the anchor, which can be spread under the influence of a spreading element. This allows the two anchor sections to be deflected with respect to one another by an active application of the spreading receptacle, in particular during the setting procedure, and in this way they are securely brought into the unfolded position before the anchor is subject to a tensile force by means of the suture element.

In addition, it is advantageous if the anchor and/or the suture element are formed at least partially from an absorbable material that can be activated by a pulse. In this way, at least part of the anchor arrangement can be activated by means of a pulse after a successful repair, in order to then be removed in the body. Depending on the type of material used, the pulse can for example be a magnetic, temperature or light pulse. This enables a largely complete healing of the body region concerned without residues of the anchor arrangement.

In a further advantageous embodiment, at least one of the anchors is at least partially formed from a shape-memory material, that can be activated by light, temperature or an electrical or magnetic field. This allows the anchor sections concerned to be deflected into the unfolded position without the application of force. In addition, the point in time at which the anchor assumes the unfolded position can be freely determined by the person setting the anchor arrangement. It is particularly advantageous if the shape-memory material comprises at least two deformation sections, which can be deformed one after the other into a respective end position. In this way, a specific sequence can be specified, in which different sections of the anchor are deflected.

Further, the above stated problem is solved by a surgical instrument for surgical tissue repair, such as in particular for repair of a meniscus tear, that is used for setting an anchor arrangement in one of the above stated embodiments. The surgical instrument comprises a hollow needle, which has a needle tip formed at a distal end, and an ejection device comprising an injection element that can move inside the hollow needle. By means of this ejection element, the first and second anchor can be moved along the hollow needle, wherein at the needle tip, the hollow needle has a closed circumferential or closable cross-section, i.e. the cross-section of the hollow needle at the needle tip is formed either materially closed or circumferentially closed by means of at least one splice. In addition, at least at the needle tip, the hollow needle has a cross-section that deviates from a circular profile, preferably a circumferential convex cross-section, such as in particular an elliptical, oval, egg-shaped or heart-shaped cross-section, or a polygonal cross-section which in particular approximates to one of these shapes. The circumferentially closed needle tip allows the stress during setting on the tissue to be repaired to be reduced to a minimum. In particular, the closed design of the needle tip prevents, as far as possible, separation of tissue particles when penetrating the tissue, which enables quicker tissue healing. In addition, the closed design of the needle tip enables greater stability of the hollow needle overall. Through the cross-section deviating from a circular profile, the tissue, which is penetrated by the hollow needle in order to set the anchor, can exert a certain resistance against rotation of the hollow needle in order to maintain the longitudinal axis thereof, such that on penetrating the tissue, the hollow needle guides itself through the tissue to a certain degree. In addition, the cross-section of the hollow needle which deviates from a circular profile and the matching guide surface of the anchor ensure an exact guidance of same in a predetermined rotation position. Due to this predetermined rotation position of the anchor with respect to the hollow needle, during the setting procedure the user can eject the anchor in such a way that it unfolds along a desired direction. In addition, through this shaping, a higher bending stiffness of the hollow needle can be obtained at least with respect to one reference plane. The hollow needle can be formed for example materially closed and comprise a longitudinal groove for at least partially receiving the suture element. Through this receiving of the suture element in a longitudinal groove provided for same, fault-free guidance of the anchor is possible inside the hollow needle. In addition, the closed design of the hollow needle can ensure a particularly high bending resistance of same over the entire length thereof.

In an advantageous embodiment, the hollow needle comprises a longitudinal slot as an alternative to or in addition to the longitudinal groove, wherein two opposite edges of the longitudinal slot lie opposite one another, at least at the needle tip, in the unloaded state. In this way, a closed hollow needle can be provided, the longitudinal slot of which is only occasionally open, in order for example to allow the setting of the threads together with the anchors. Through the adjacent edges, the hollow needle can maintain a relatively high stability despite the slot, and unwanted ingress and separation of tissue material during pricking is prevented.

It is advantageous if the edges widen by means of pressing a section of the suture element or a section of the anchor, through which the longitudinal slot is slightly opened during the movement of the anchor along the hollow needle and the hollow needle is otherwise closed. It is advantageous if the hollow needle is curved towards the needle tip, due to which, during certain applications of the surgical instrument, a region of the tissue concerned intended for setting the anchor can be made more easily accessible.

In a particularly advantageous embodiment of the surgical instrument, the needle tip is closed in a flush manner by the first and the second anchor of an anchor arrangement received therein according to one of the above-described embodiments. In this way, the at least two anchors provided for setting, can close the hollow needle of the surgical instrument in a similar manner to a plug and thus prevent tissue particles from entering the hollow needle at the needle tip during penetration of the tissue and from being separated from the rest of the tissue. For this purpose, the anchor has a chamfer at the distal end, which has an angle of incidence with respect to a longitudinal axis of the base body that matches the distal needle tip. In this way, the anchor can form together with the needle tip a closed distal end of the hollow needle, via which no tissue particles can enter into the hollow needle during pricking and penetrating of a tissue. This determines whether the at least two anchors can be unfolded with respect to an angular position specified for an application of the surgical instrument with regard to a setting axis in the vertical direction or alternatively in the horizontal direction. A preferred unfolding direction is selected depending on the application, by means of which an optimised attaching of the anchors can be achieved on the tissue concerned.

Furthermore, it is advantageous if the ejection element comprises spreading means at a distal end in order to impinge on the proximal end of the first anchor and/or of the second anchor. This makes it possible to apply spreading forces at the proximal ends by means of the ejection element, in particular to anchors comprising at least two anchor sections that are movable relative to one another. In this way, the at least two anchor sections can be actively spread or unfolded during the setting procedure by the ejection element, in order to prevent a re-entry into the hollow needle or into the passage in the tissue created by the hollow needle.

Advantageously, the spreading means have a tapered region at the distal end of the ejection element, which is movable between the two anchor sections of the first anchor and/or of the second anchor. In this way, the anchor sections of an anchor, which are moveable relative to each other, can be moved away from each other or spread, simply by pressing the tapered region at the proximal end of the anchor concerned.

Alternatively or in addition, the spreading means comprises at least two elastic spreading arms arranged at the distal end of the ejection element, which can be prestressed away from each other in contact against the anchor sections of one of the anchors. Through such pretensioned spreading arms, a secure spreading or unfolding of the two anchor sections which are moveable relative to each other can be ensured during setting of the anchor. In an alternative embodiment, the ejection device comprises a separate ejector for the first anchor and for the second anchor, wherein, for example, an individual ejection mechanism or individual actuation element is provided for each anchor.

In a further advantageous embodiment of the surgical instrument tensioning, means are provided on the hollow needle for tensioning the suture element. Such tensioning means make it possible to avoid faults or an additional separation of tissue particles due to the suture element transported on the hollow needle, in particular during penetration of the tissue to be repaired.

It is advantageous if the tensioning means comprises a slider element moving along the hollow needle, on which the suture element is deflected and which is pretensioned in the proximal direction. This allows the suture element to be held in the hollow needle in a particularly space-saving manner and allows the anchor to be easily released during setting.

Advantageously, at the needle tip, the hollow needle has a distal section and a receiving section arranged proximal thereto, which is formed with an enlarged cross-section with respect to the distal section. This allows the distal section to be designed as thin as possible, in order simply to be able to move the anchors to the needle tip and also to accommodate parts of the ejection device in the proximal receiving section next to the anchor or anchors received therein.

Thus it is particularly advantageous if, in the enlarged cross-section, the ejection element can be guided past the second anchor. In this way, for example, the first anchor can be moved by means of the ejection element along the distal section to the needle tip and ejected there, while the second anchor, and where relevant further anchors, can remain in a passive position in the proximal receiving section. Alternatively, it is also possible that the proximal section is connected to a handle receptacle of an instrument handle, in which at least one anchor can be received beforehand. In this way it is possible to store a plurality of anchors on the surgical instrument and to shield these where necessary against external influences. This also allows, for example, anchors to be transported by the surgical instrument that comprise shape-memory material that can be activated by temperature, light or electricity. Thus it is advantageous if the at least one anchor is formed by a pretensionable anchor and can be received in the proximal receiving section of the hollow needle or in the handle receptacle, in a tension-free position. This makes it possible to transport the anchor in the surgical instrument over a relatively long time before the setting, without the elastic means, by means of which the pretension can be produced and which for example is formed by a spring element or an elastic material section, being able to relax. The anchor is stored in an at least approximately tension-free position in the handle receptacle and brought into the respective pretensioned position only shortly before the setting procedure thereof, in which it can be moved to the needle tip along the hollow needle. It is also advantageous if the at least one anchor can be moved from the handle receptacle into the proximal section, by which means the anchor can be transferred in a particularly convenient manner from the stored position in the handle receptacle into an active position inside the hollow needle, out of which it can be moved by means of the ejection device, without requiring the anchor to be removed manually, for example, from the handle receptacle.

In addition, it is advantageous if the proximal receiving section is provided with securing means, by means of which the second anchor can be supported in both axial directions. This allows the second anchor to be securely held in the passive position during a setting procedure of the first anchor, in order to avoid disturbances during setting of the first anchor.

A particularly advantageous embodiment of the surgical instrument comprises a toothed gearing for controlling the movement sequences of the ejection device. In this way, the individual movement sequences for sequential setting of the at least two anchors, such as for example the movement of the second anchor into a setting-ready position following setting of the first anchor, or the distal and proximal movements of the at least one ejection element, can be exactly controlled in terms of the sequence or temporal progression thereof. The ejection device can be actuated by means of an actuating element arranged adjacent to the instrument handle, which can be moved manually from a starting position into a set position. In this way, the ejection device can be manually controlled by the operator during the entire setting procedure.

Thus it is advantageous if the toothed gearing has a specified ratio between an actuation element that can be moved manually or by means of a force memory and the ejection element. In this way, depending on which movement speed results from the expected application of force, a particularly suitable movement speed of the ejection element can be specified. Alternatively, it is also possible, for the ratio to be set between the actuating element and the ejection element, wherein in particular one of a plurality of settable ratios can be selected. Thus a person using this surgical instrument or an operator, can adjust the instrument to their personal requirements or to an intended application.

The anchors can advantageously be supported by the ejection device in the proximal direction in a setting-ready position, wherein the movement of the ejection device is locked in the proximal direction. This makes it possible to prevent the anchors from being moved in the proximal direction from the setting-ready position, in particular during pricking of the hollow needle into the tissue to be repaired, which in turn prevents tissue material from entering into the hollow needle at the needle tip.

In addition, it is advantageous if the actuating element can contact an end stop and the ejection device is thus arranged in an end stop position, which corresponds to the setting-ready position of the respective transported anchor. This allows the user to reliably visualise the setting-ready state of the respective anchor during manual actuation of the surgical instrument and prevents accidental setting of same.

Further, it is an advantage if the actuating element can be rotated from the end stop position into a release position by separating the toothed gearing, in which the actuating element is moved further in the setting direction. In this way, it is possible, after attaining the setting-ready position of the anchor to be set, to cancel the ratio acting between the actuating element and the instrument handle. Thus, for example, the movement of one anchor from the proximal receiving section into the setting-ready position can occur with a relatively large ratio and thus through a relatively small movement of the actuating element. After attaining the end stop position and rotating the actuating element into the release position, there then follows a direct movement of the ejection device via the actuating element without a gearing ratio, in order to enable the user to have better control of the setting procedure.

Advantageously, the end stop position and the release position are thus specified by a control cam on the instrument handle, into which a cam accompanying the actuation element protrudes. In this way, the end stop position and the release position can be set in a simple and accurate manner.

It is also advantageous if an ejection stop is provided, by means of which the movement of the ejection device in the distal direction can be limited, in order to avoid the ejection element being able to exit from the hollow needle or an error function arising as a consequence of an excessive force of the ejection device Advantageously, the actuating element can be moved after actuation thereof and released by means of an actuated hand by means of a reset spring mechanism, from the ejection stop position into the starting position, wherein at the same time the ejection device can be displaced behind the second anchor. As a result, during an application, the operator must simply undertake manual setting of the anchor, while after setting of the first anchor, the second anchor is automatically brought into a setting-ready position. In this way, the application of the surgical instrument is more convenient for the operator. Advantageously, a signal transmitter is provided, which is automatically activated on attaining the starting position. During an application, the operator can be given, for example, an acoustic, haptic or optical feedback, if the second anchor is in the setting-ready position. In this way, the operator obtains reliable feedback as soon as the surgical instrument is ready after setting of an anchor, in order also to be able to set the subsequent anchor.

Figure 2:
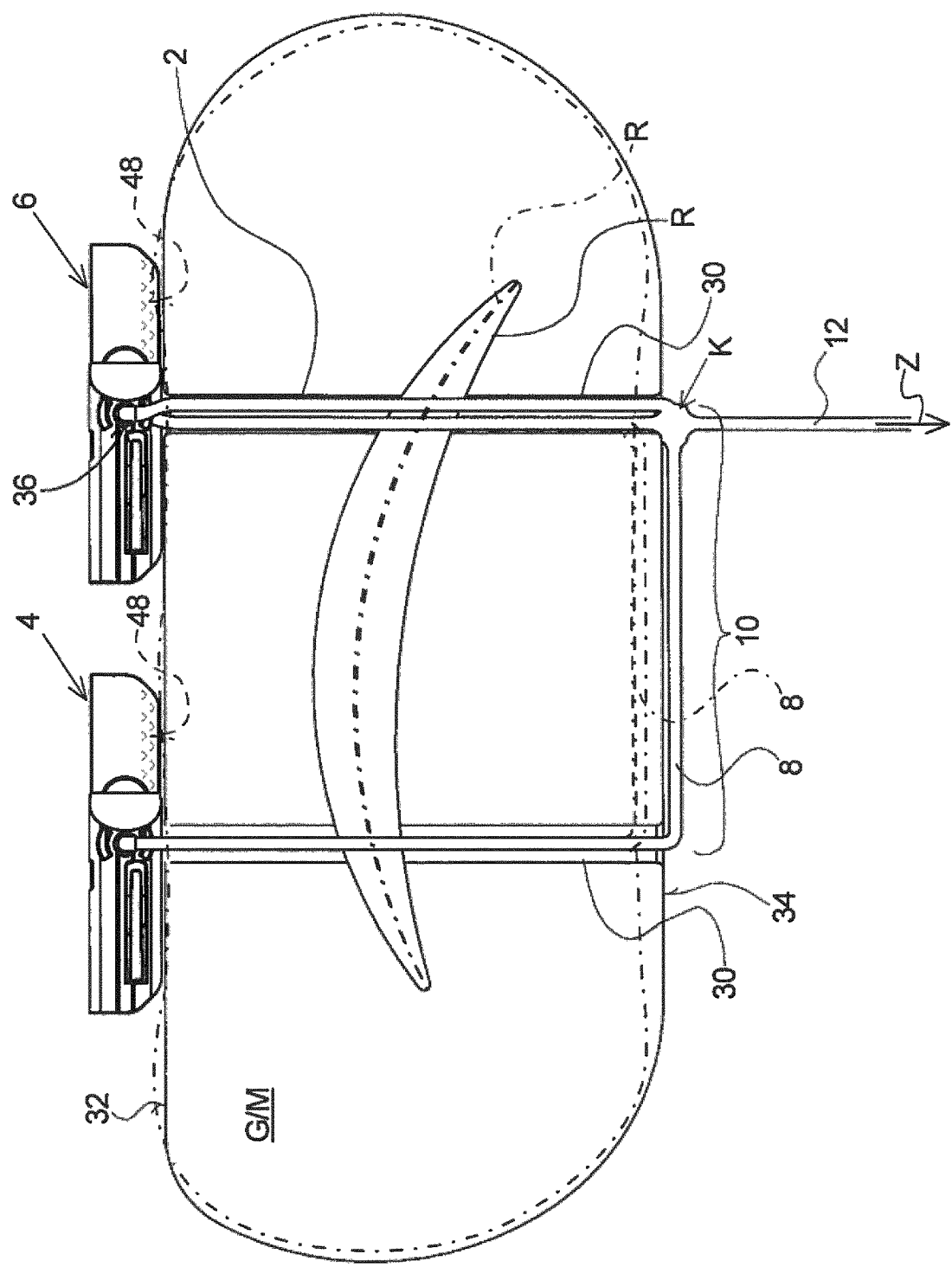
Figure 3:
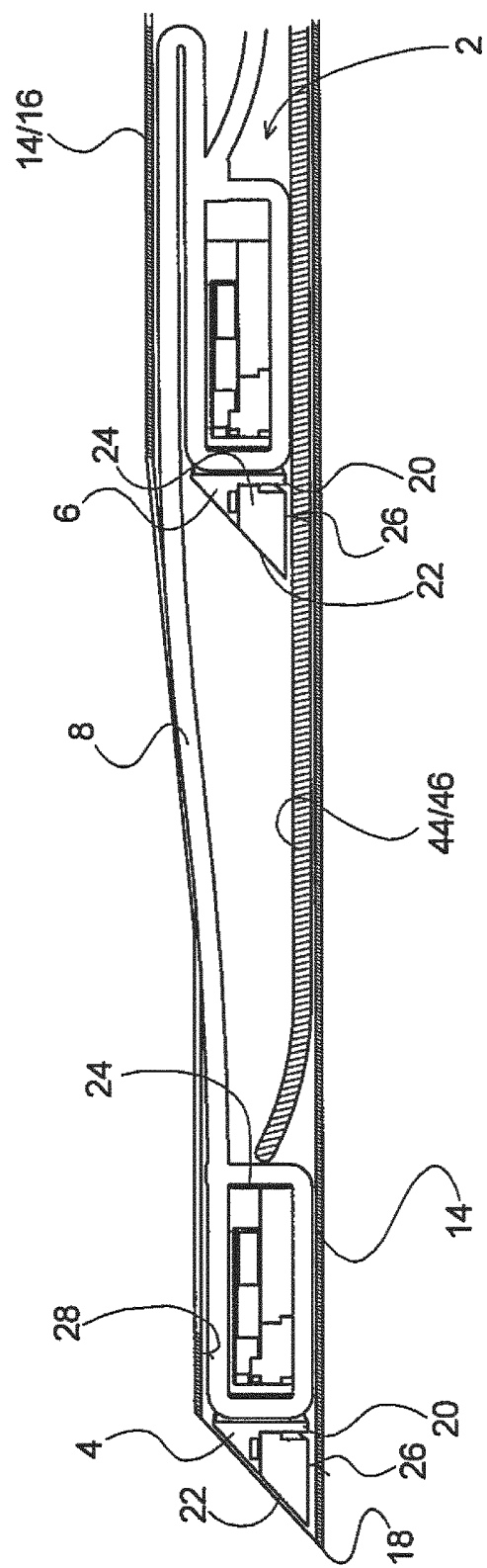
Figure 4:
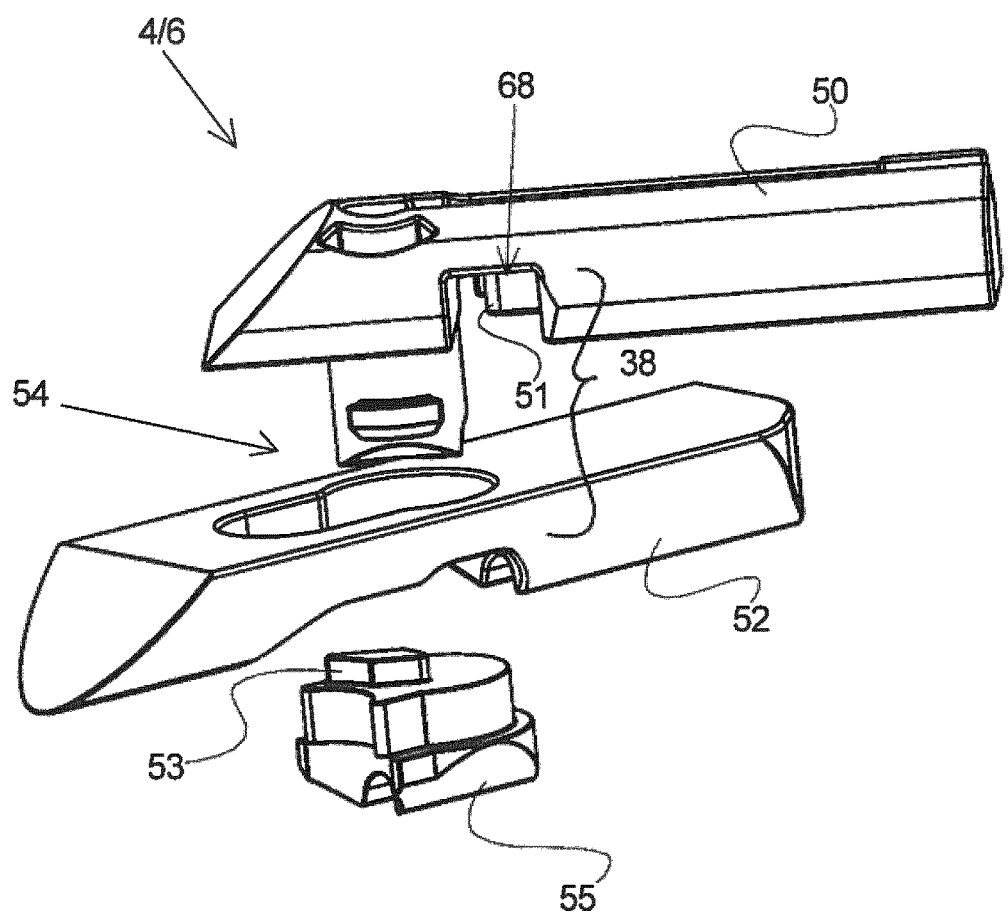
Figure 5:
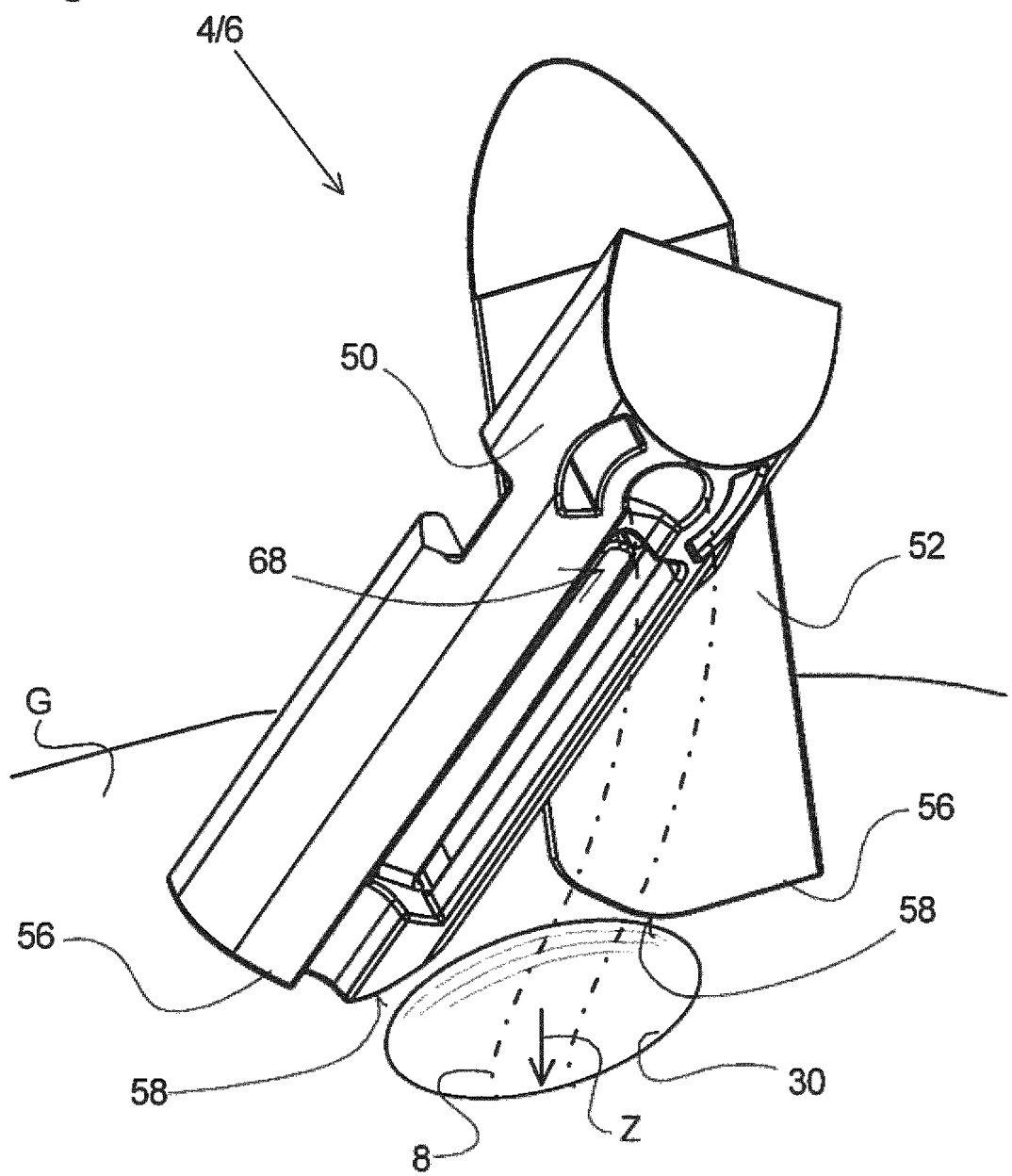
Figure 6:
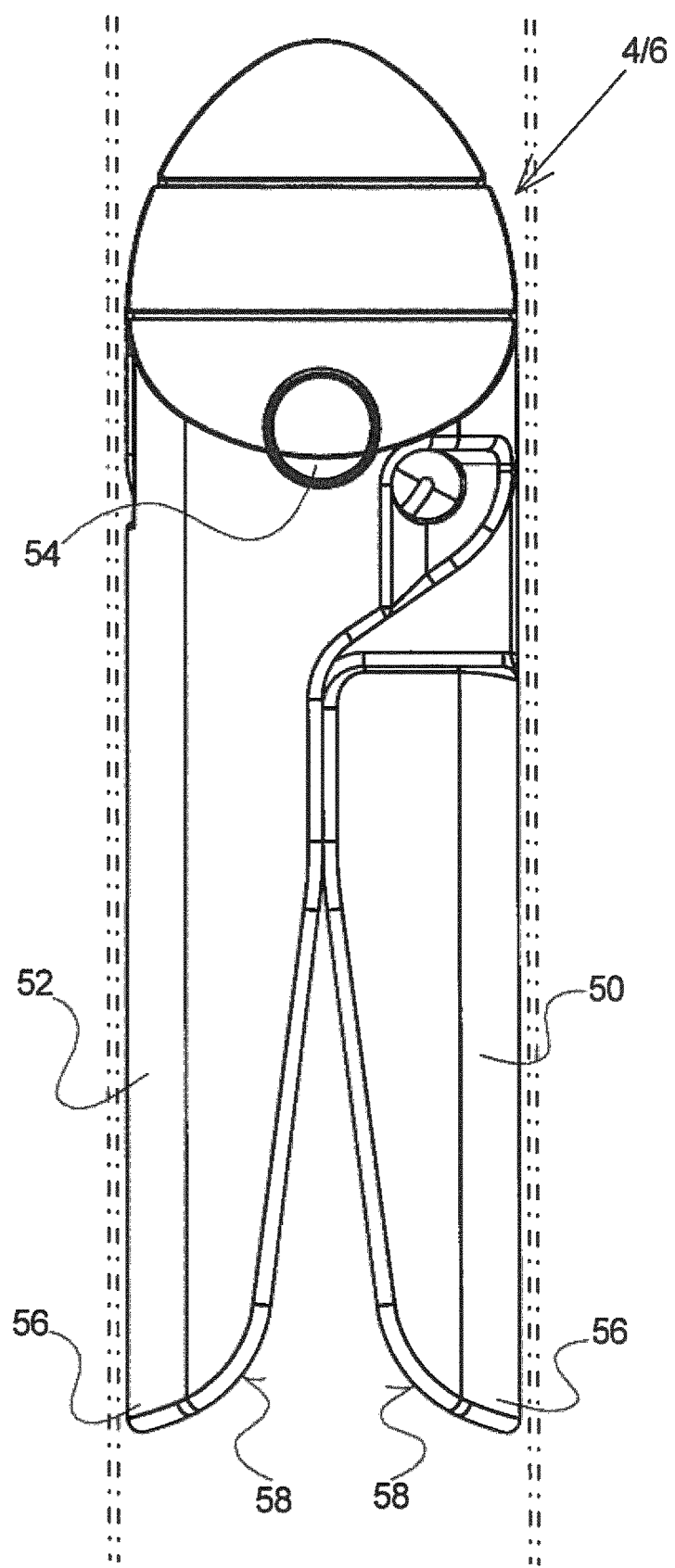
Figure 7:
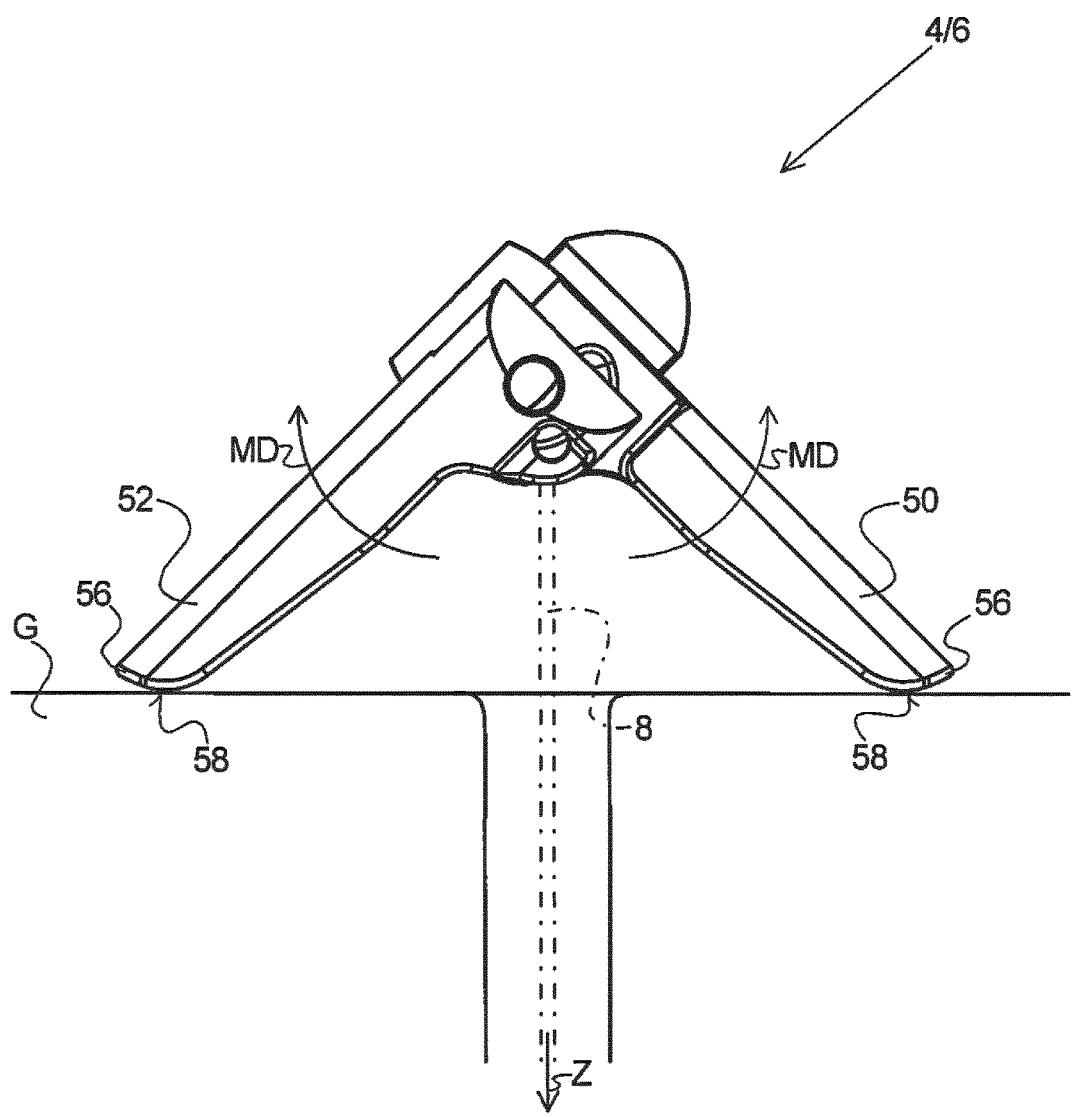
Figure 8:
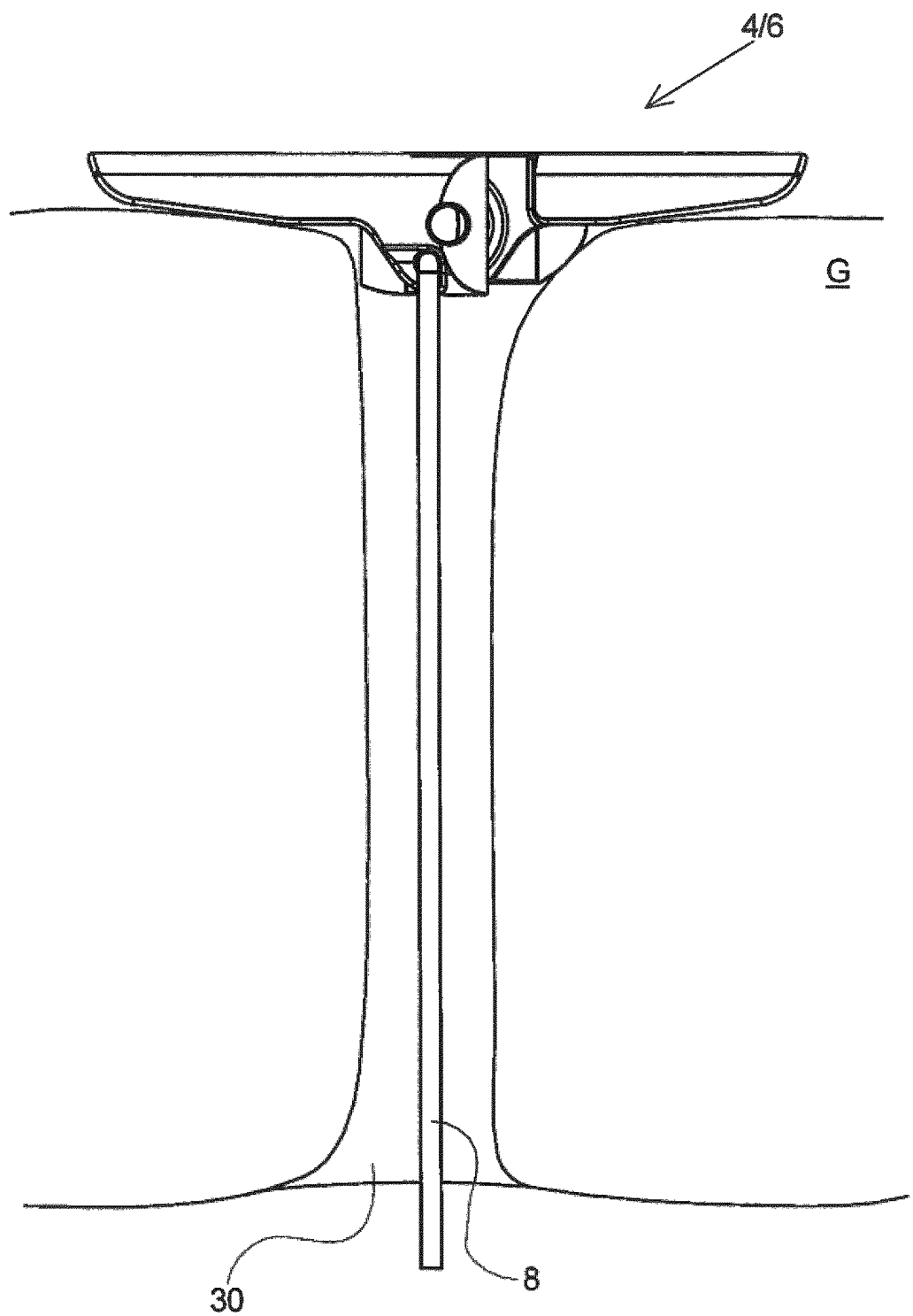
Figure 9:
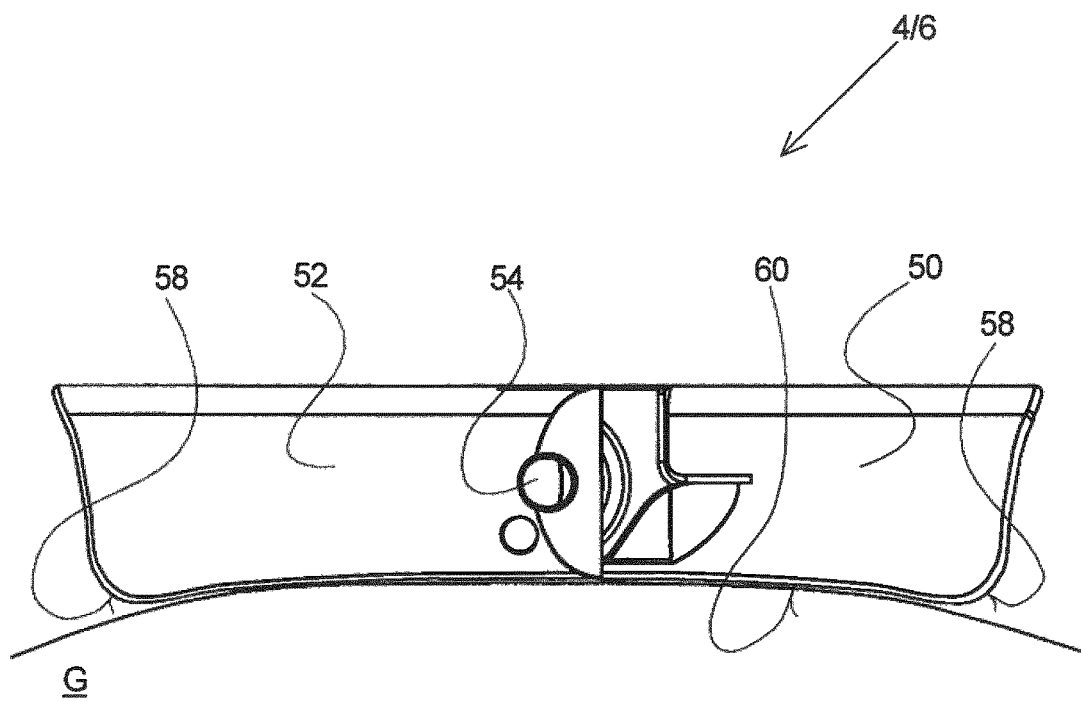
Figure 10:
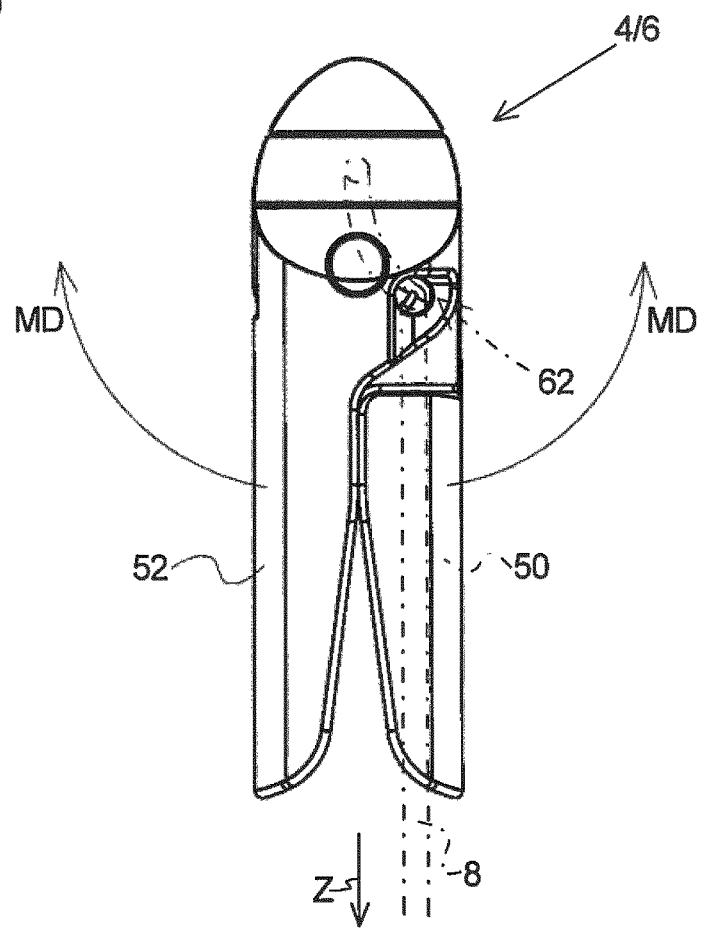
Figure 11:
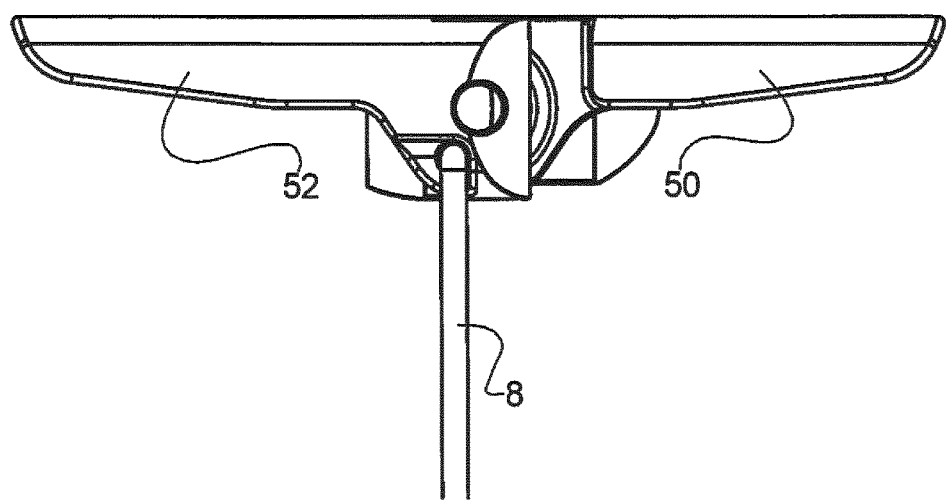
Figure 12:
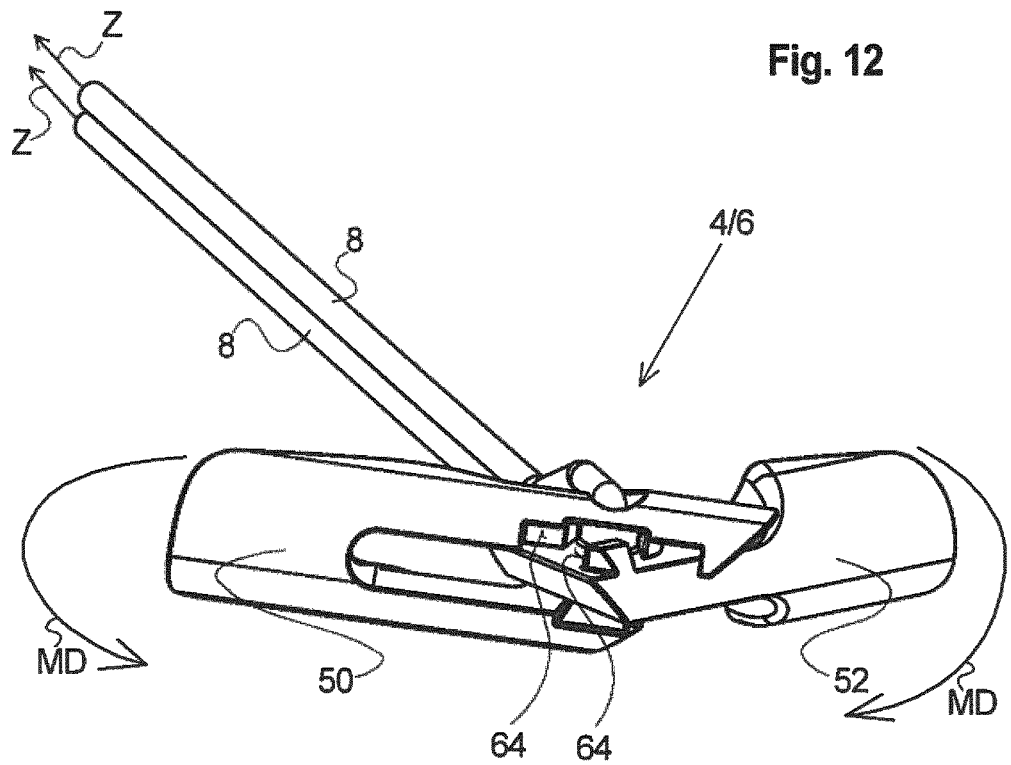
Figure 13:
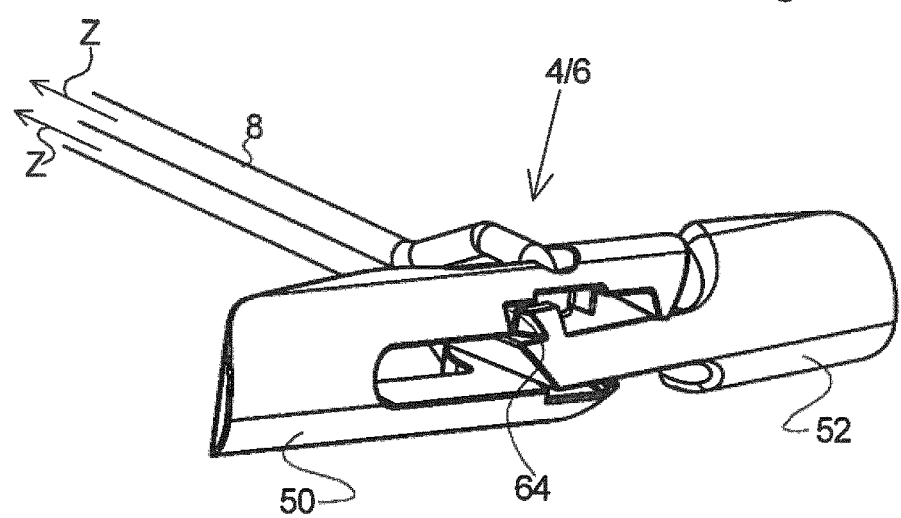
Figure 14:
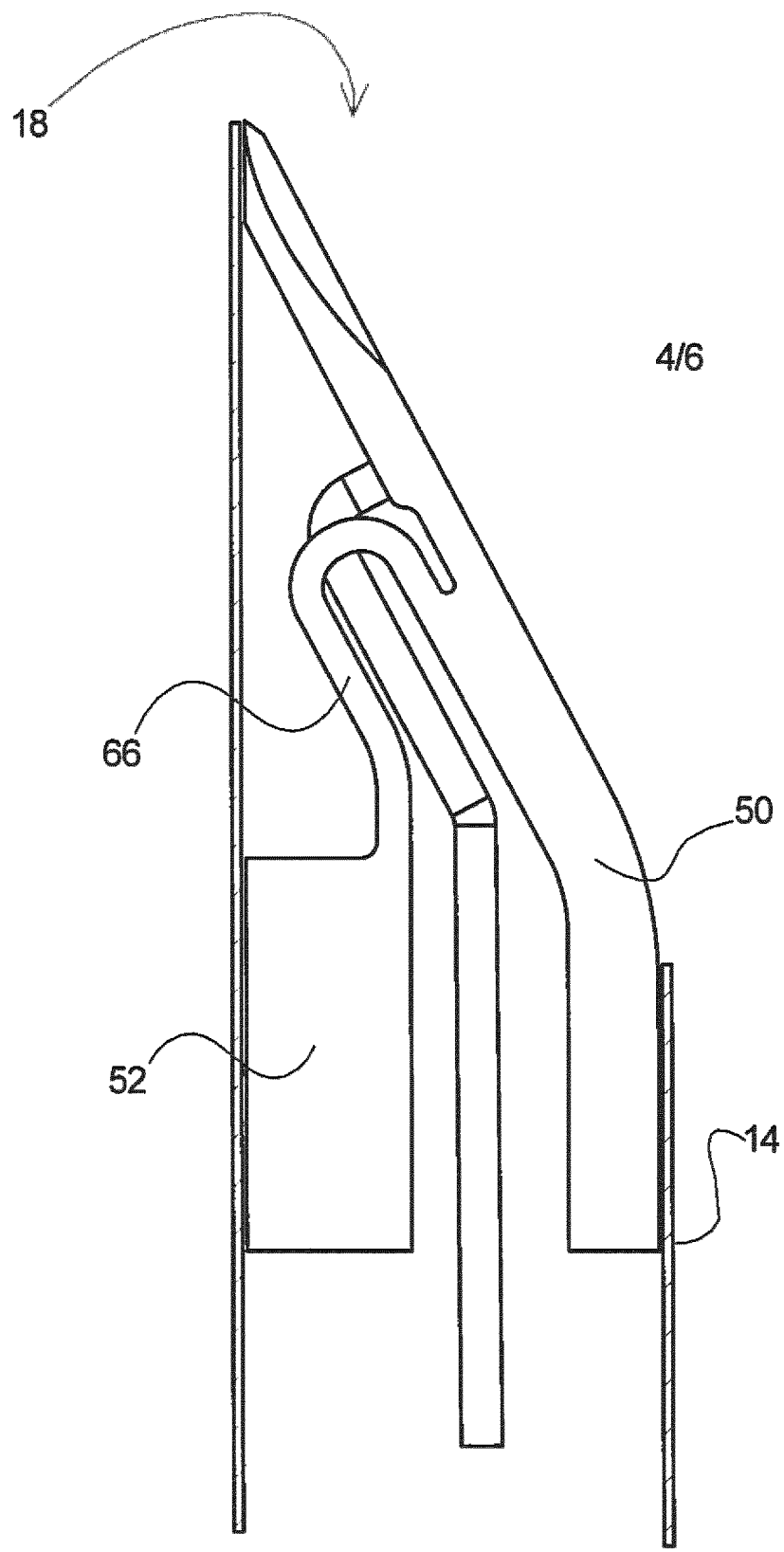
Figure 15:
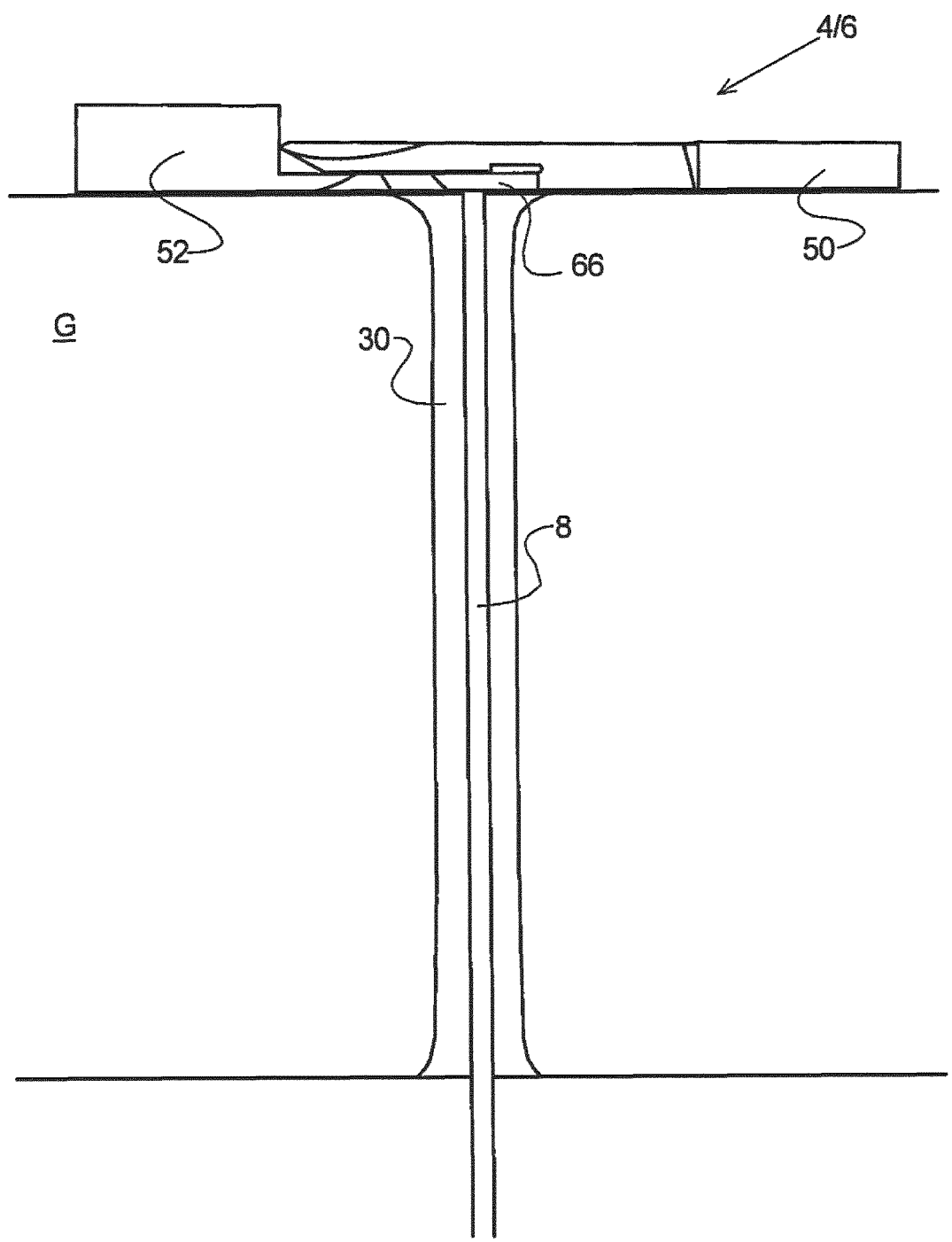
Figure 16:
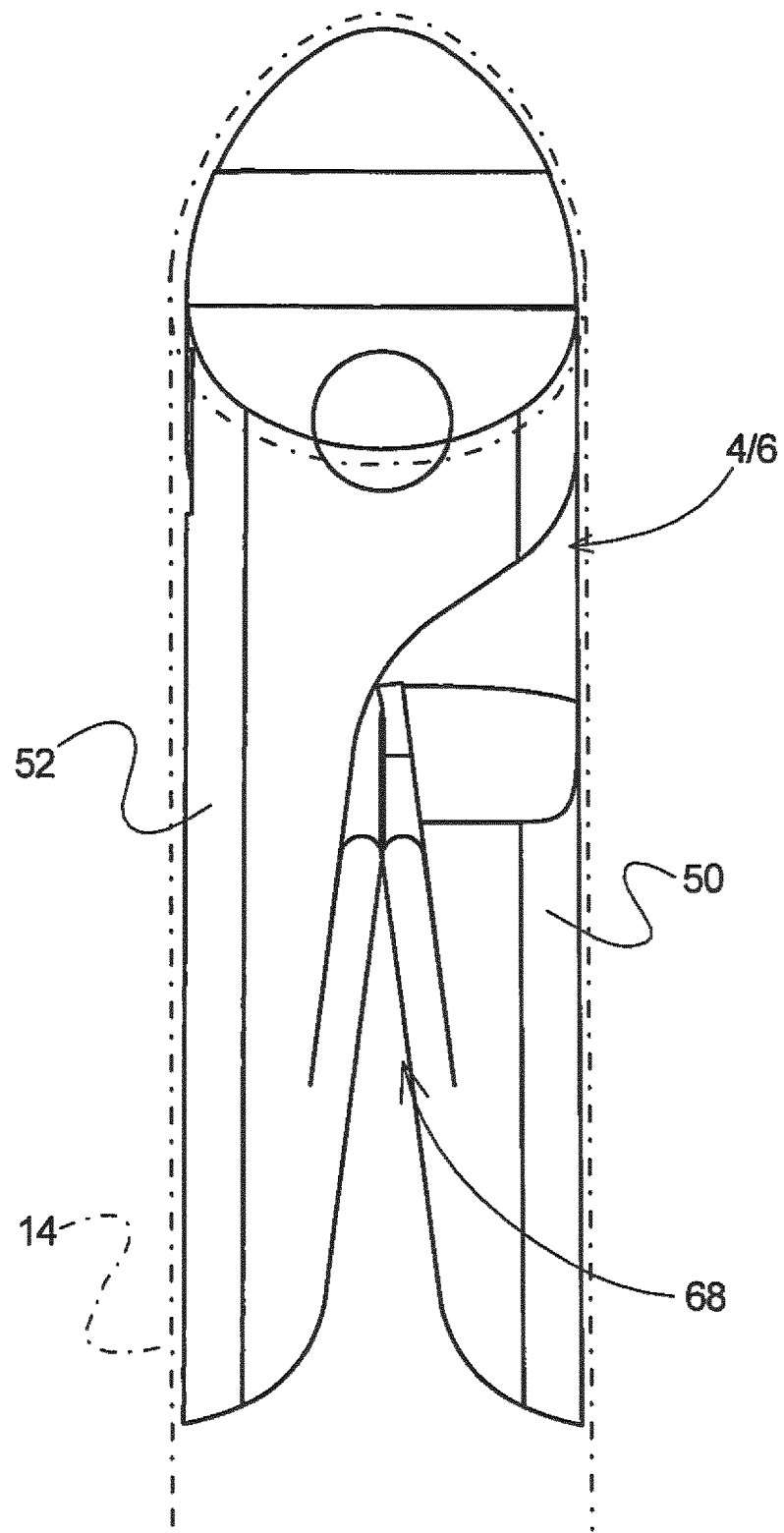
Figure 17:
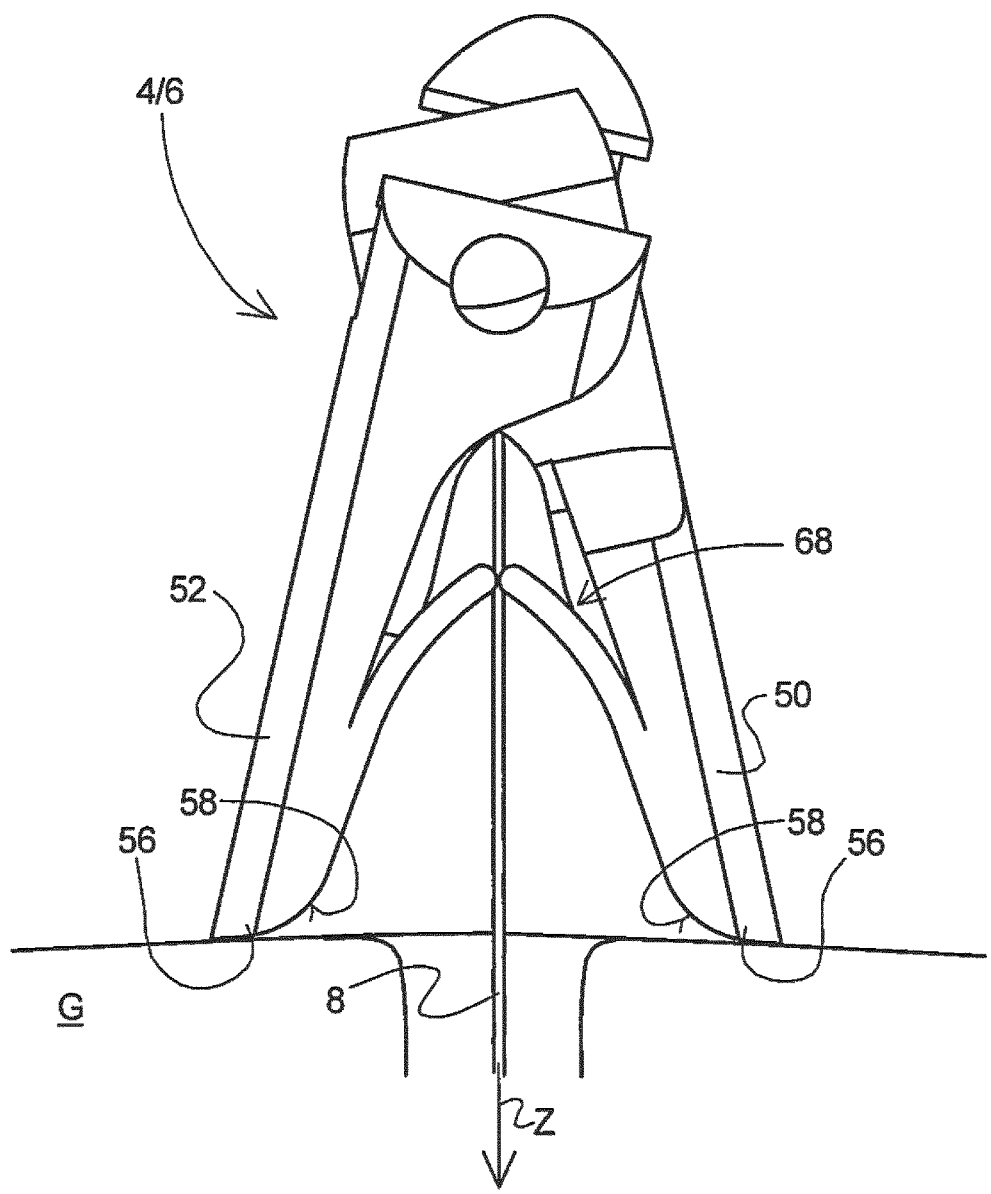
Figure 18:
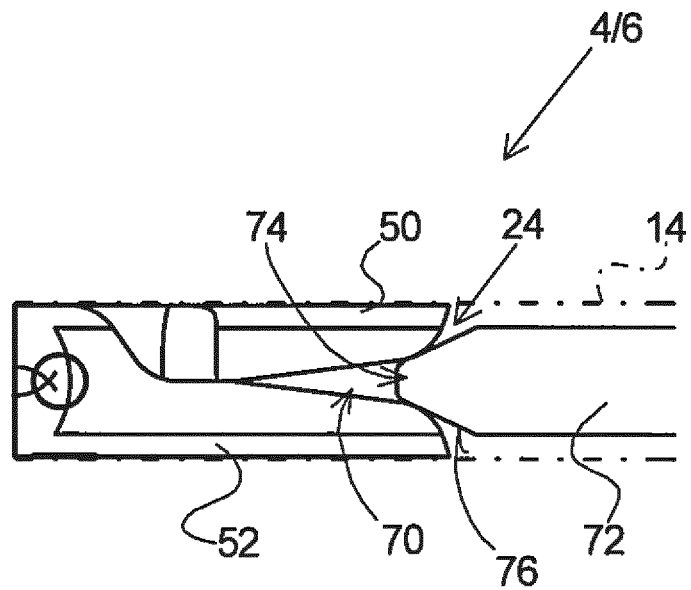
Figure 19:
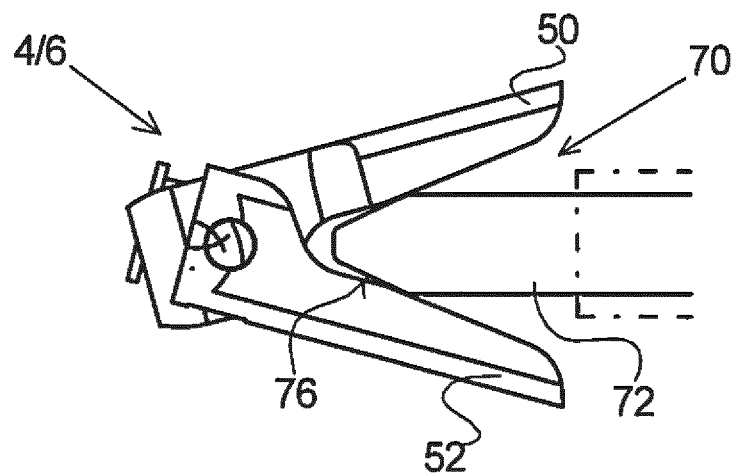
Figure 20:
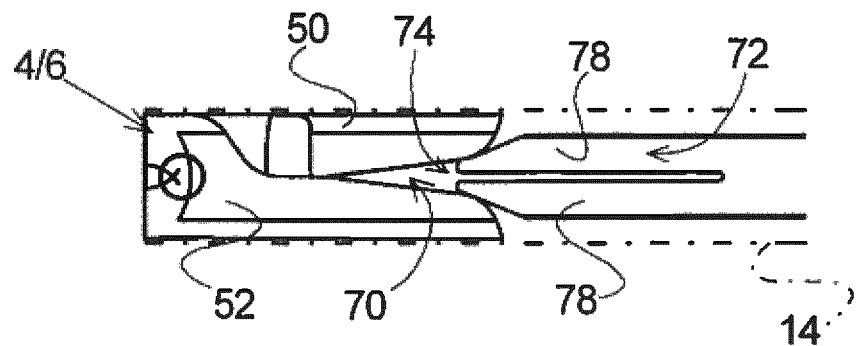
Figure 21:
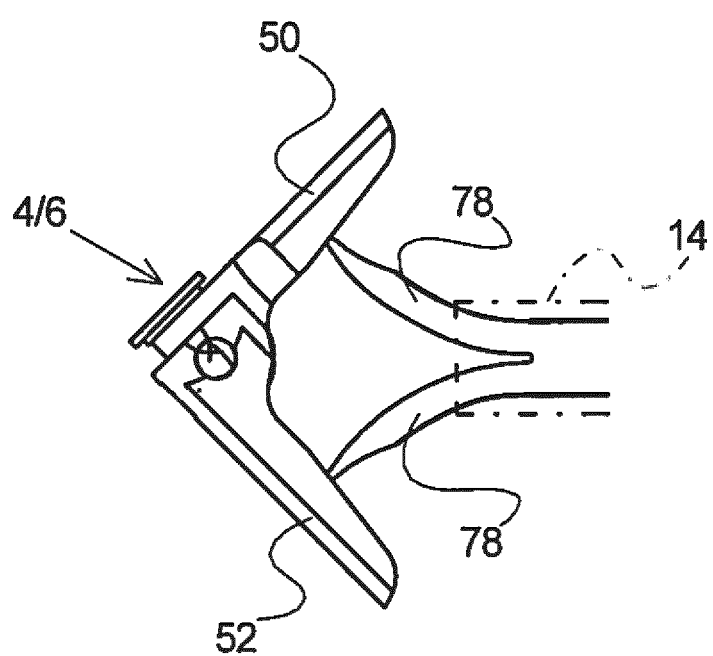
Figure 22:
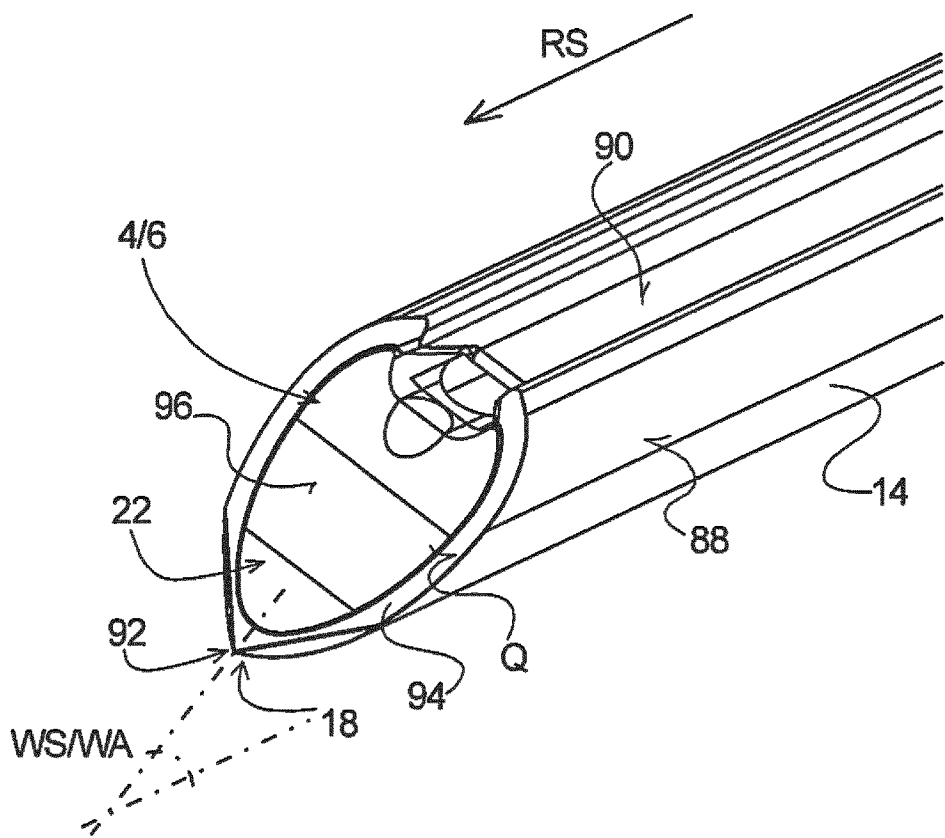
Figure 23:
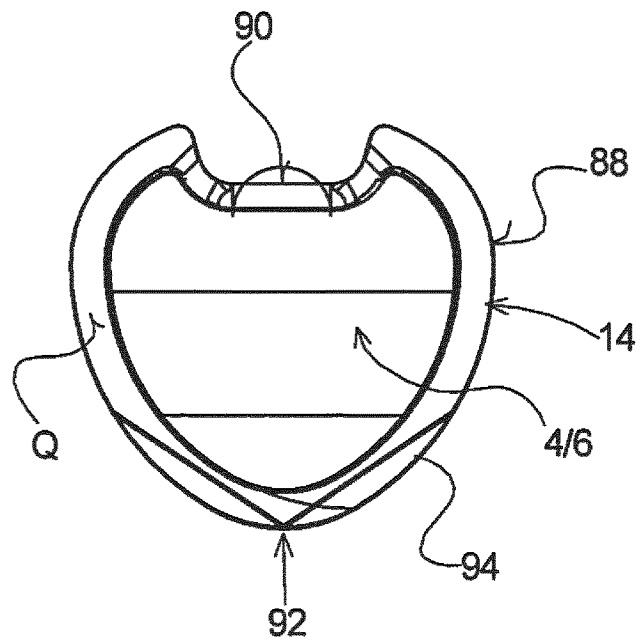
Figure 24:
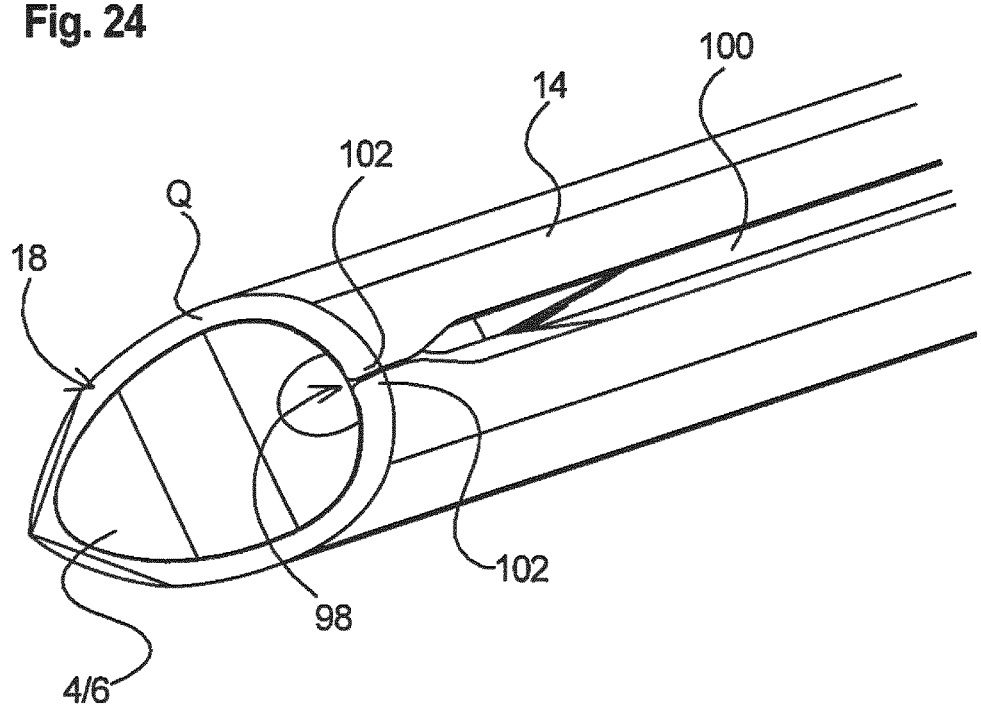
Figure 25:
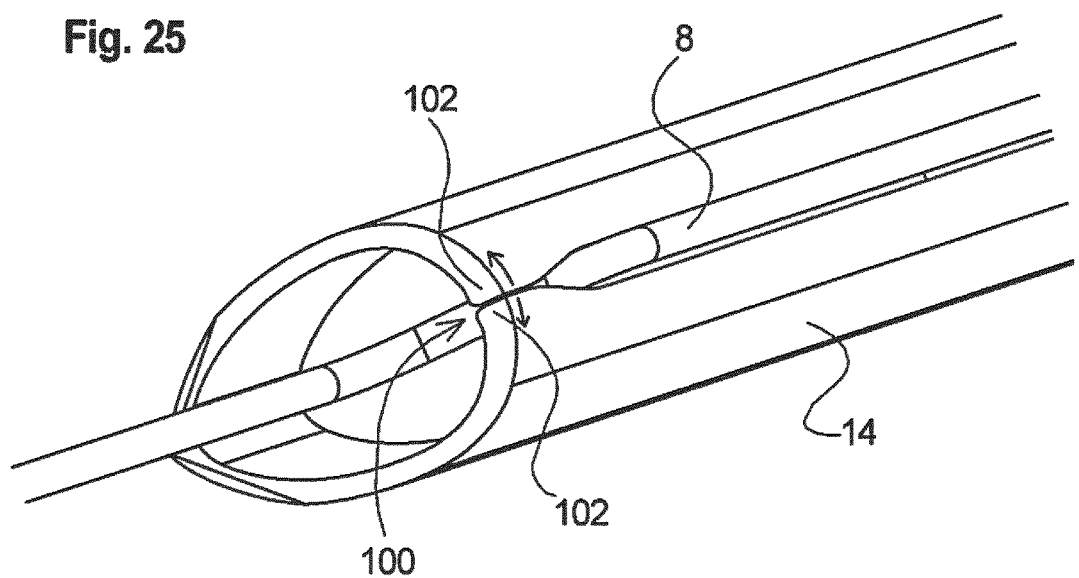
Figure 26:
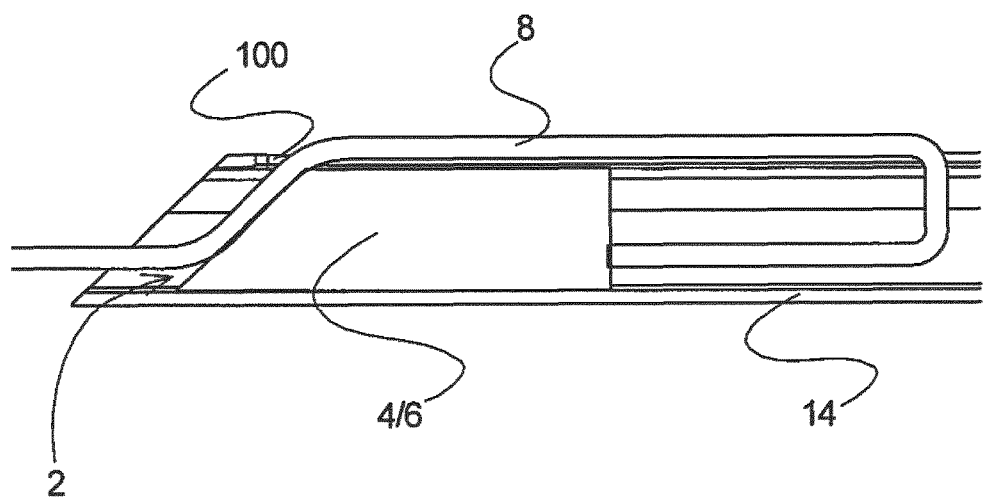
Figure 27:
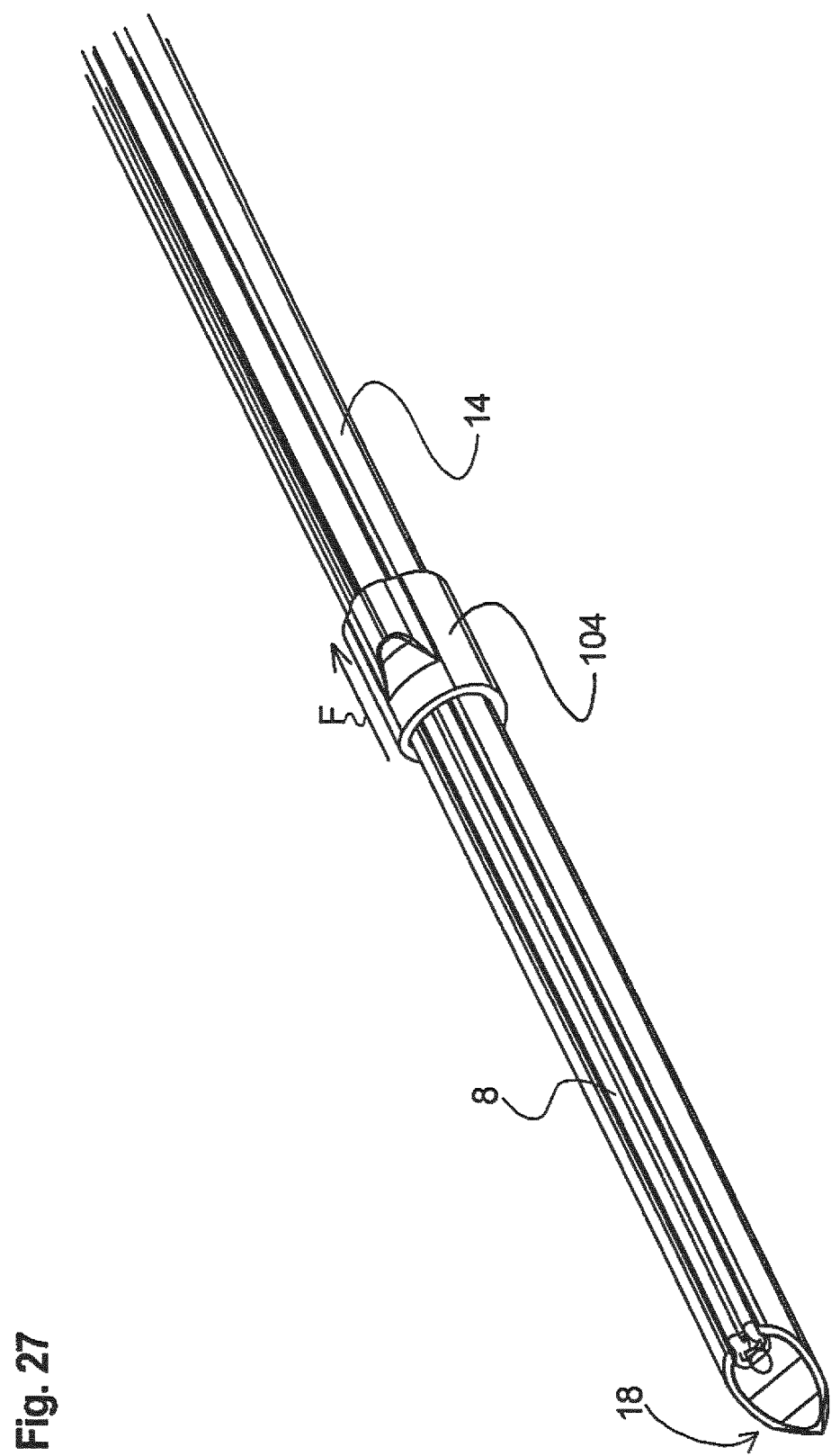
Figure 28:
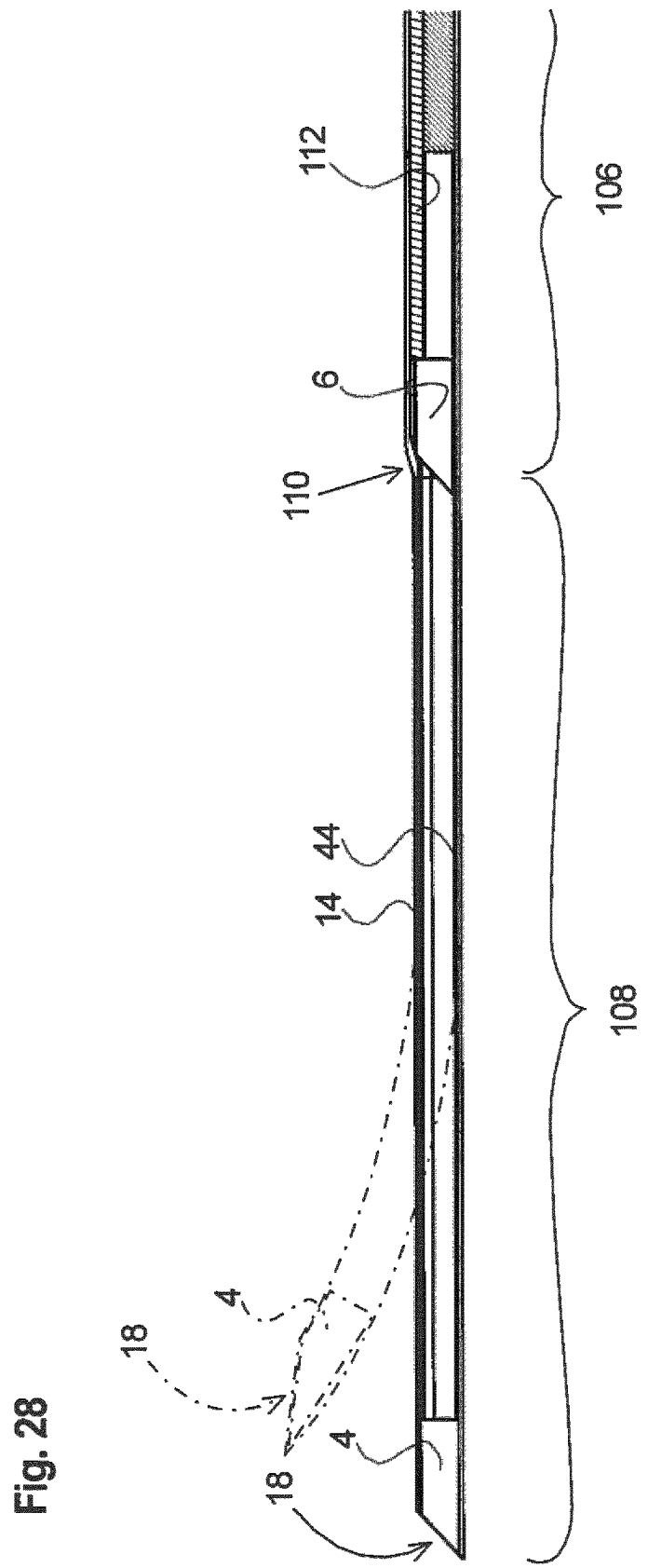
Figure 29:
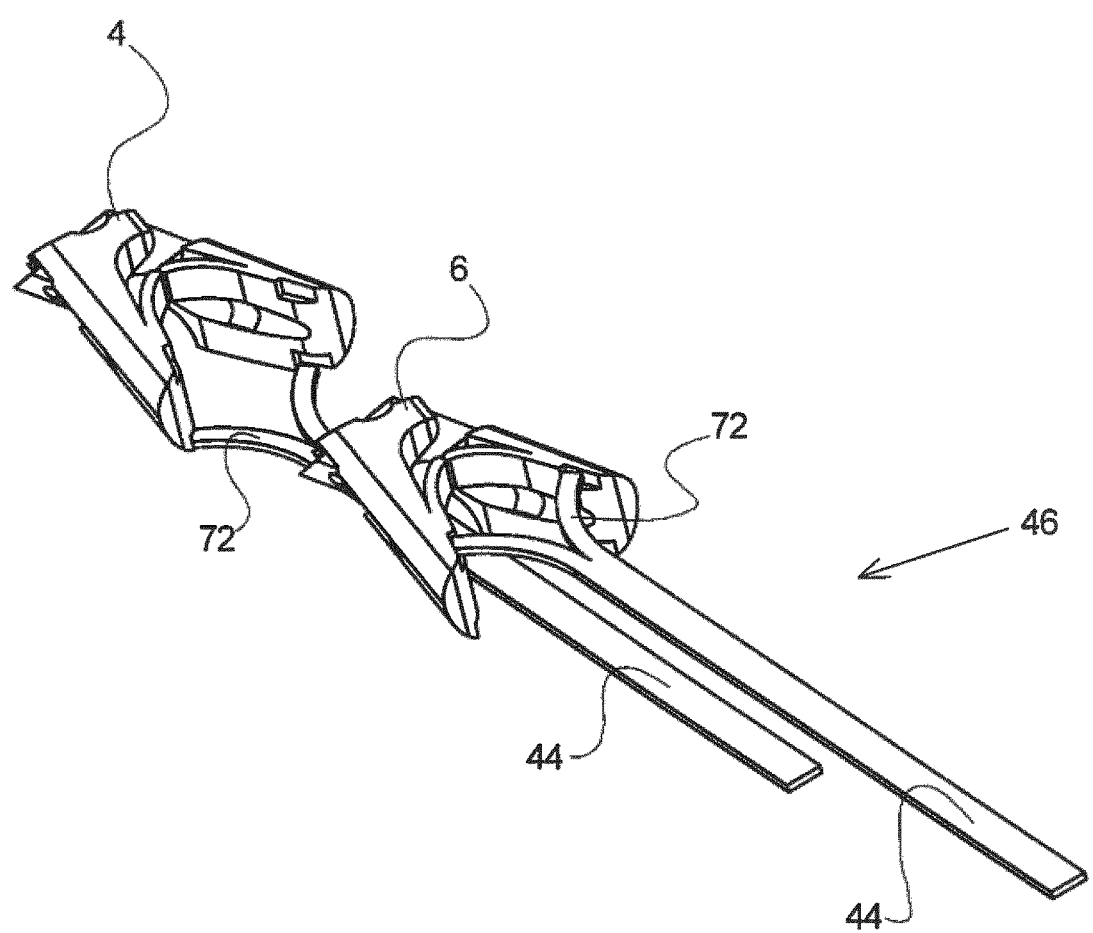
Figure 30:
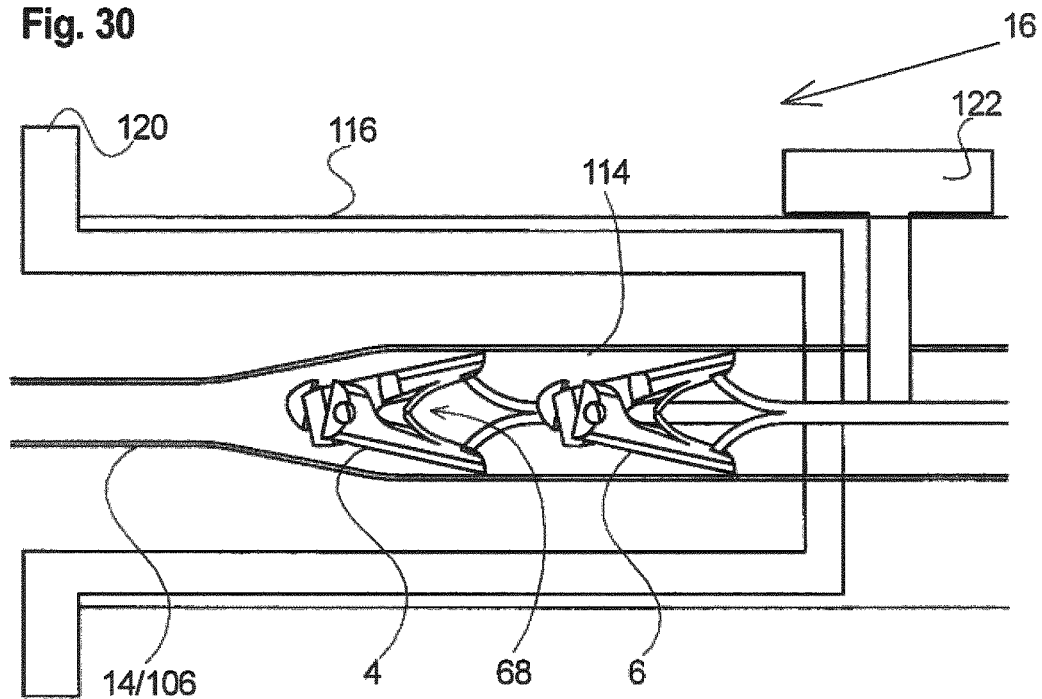
Figure 31:
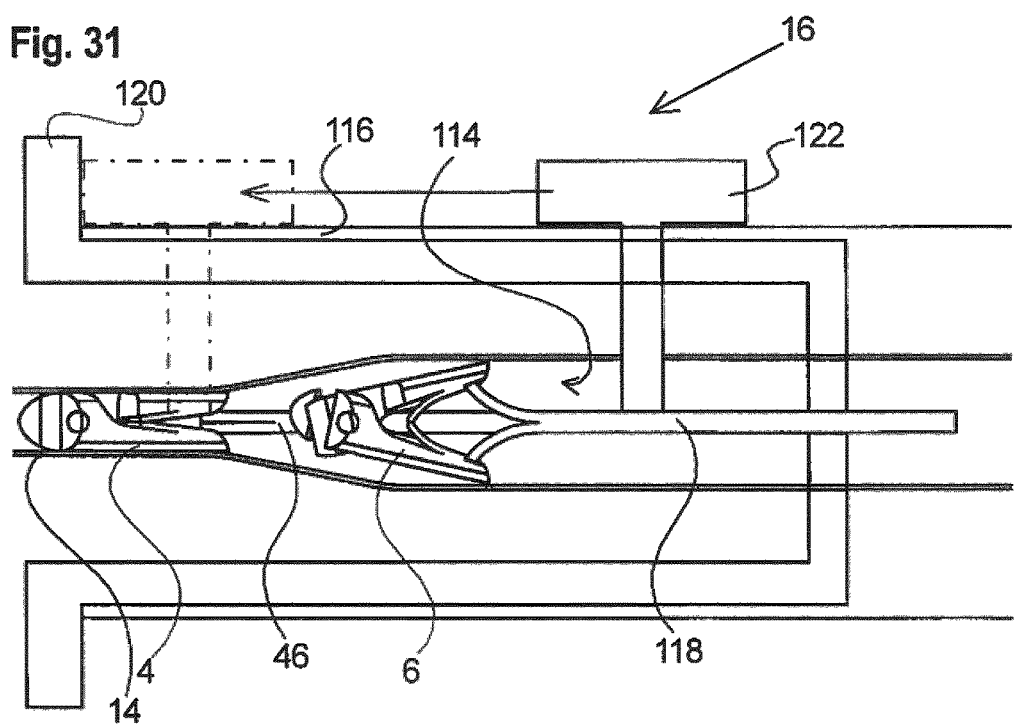
Figure 32:
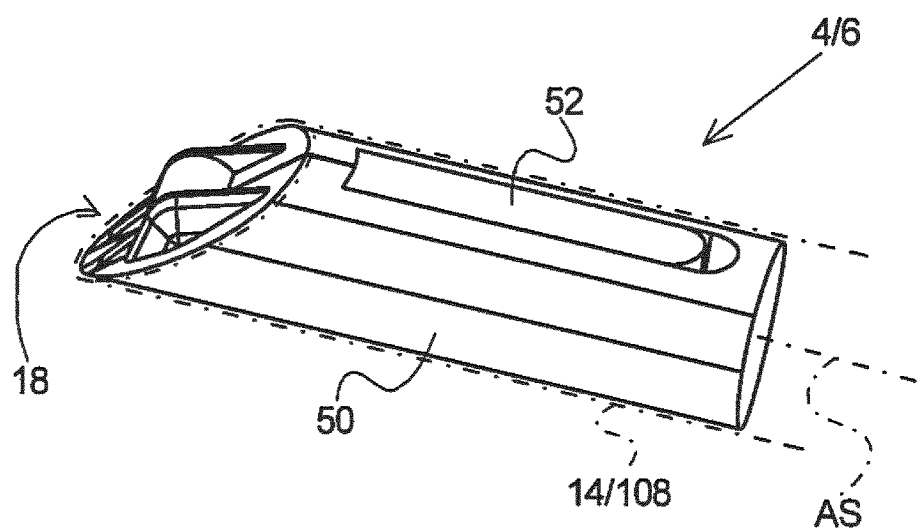
Figure 33:
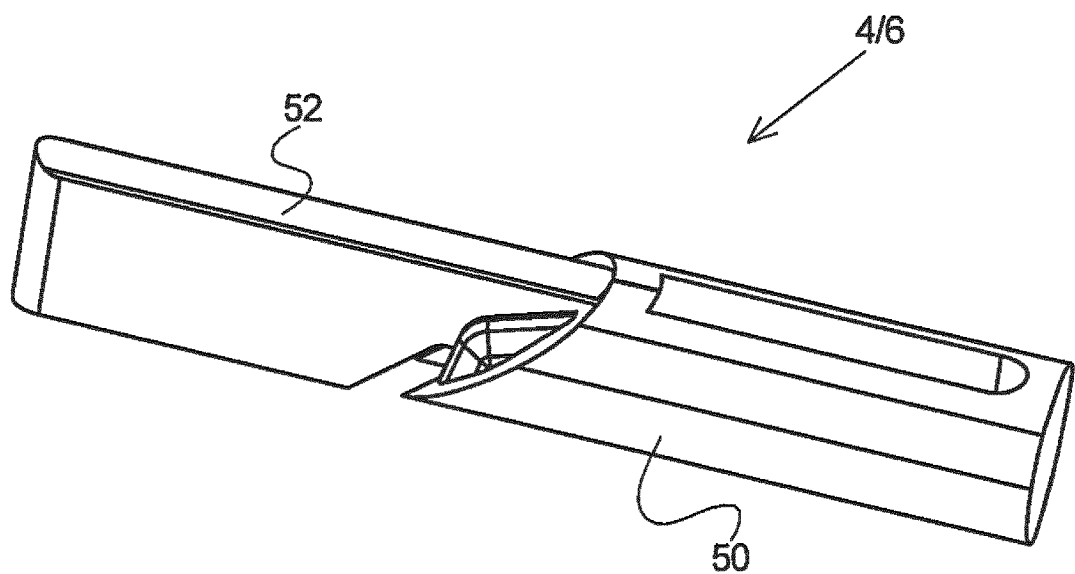
Figure 34:
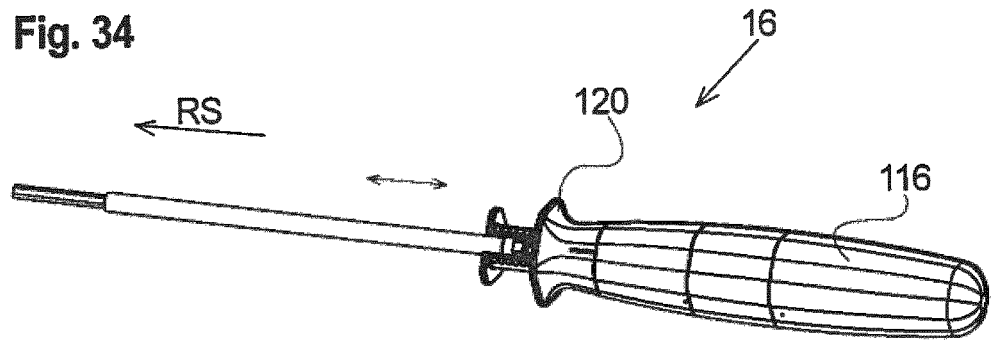
Figure 35:
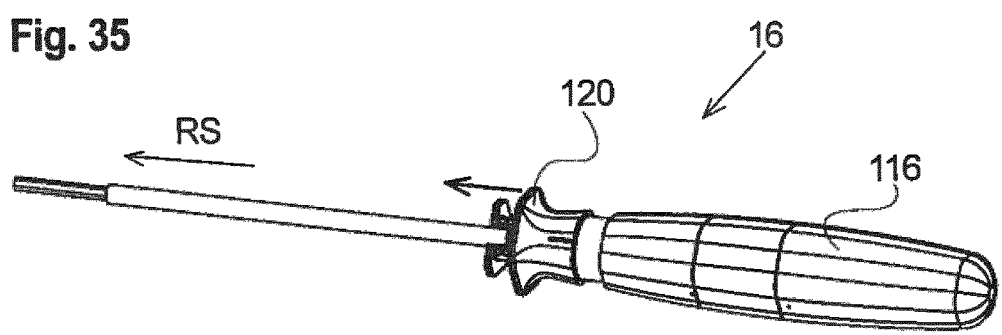
Figure 36:
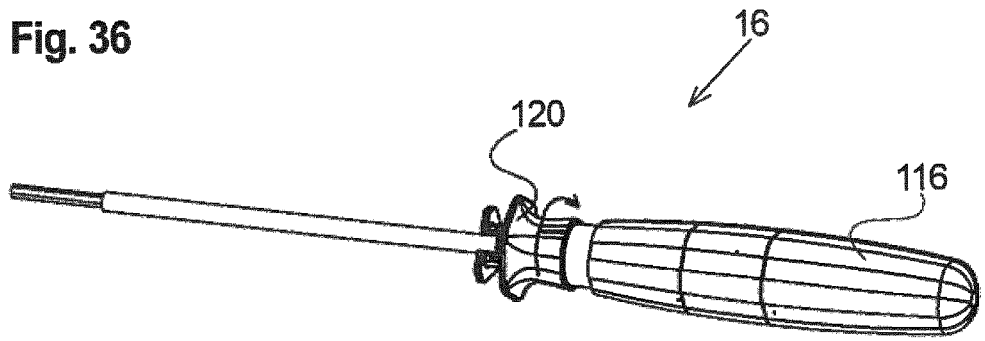
Figure 37:
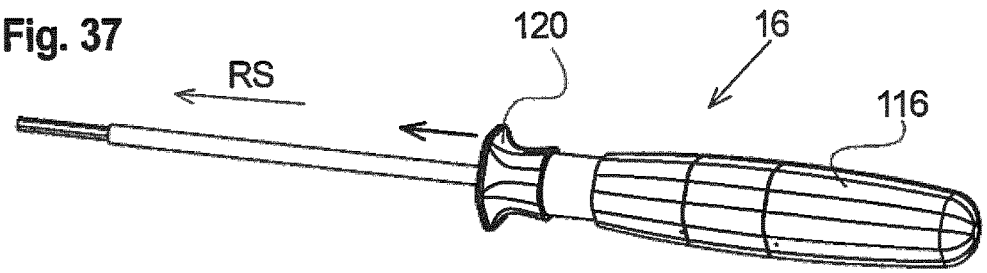
Figure 38:
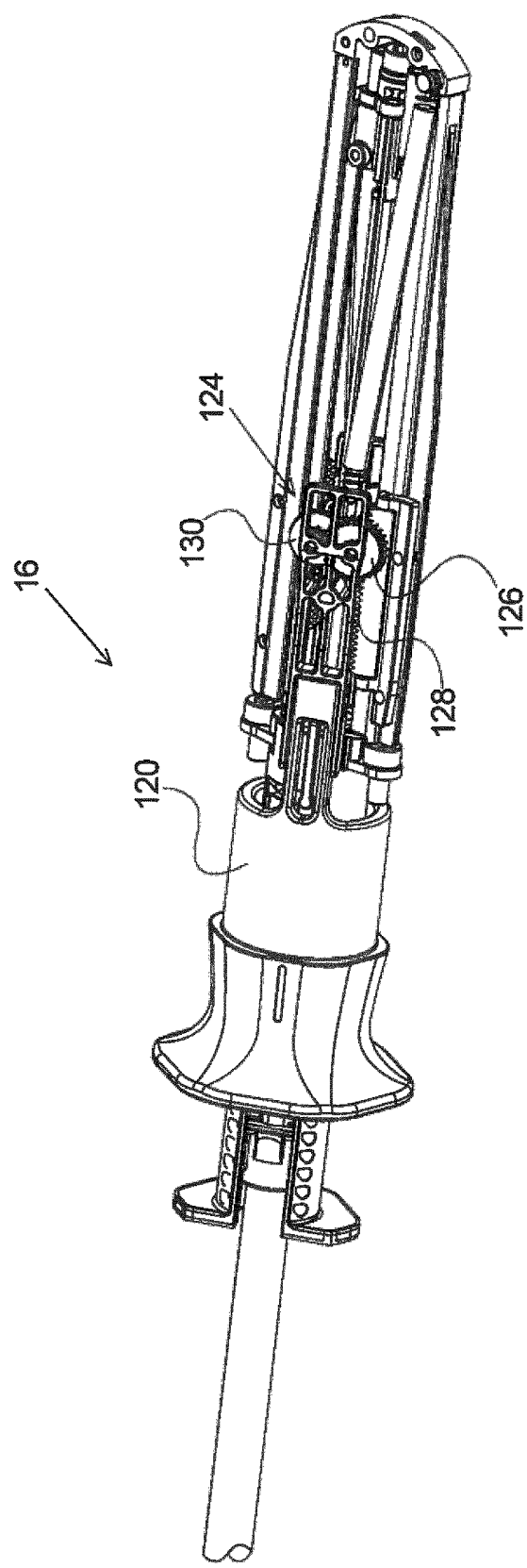
Figure 39:
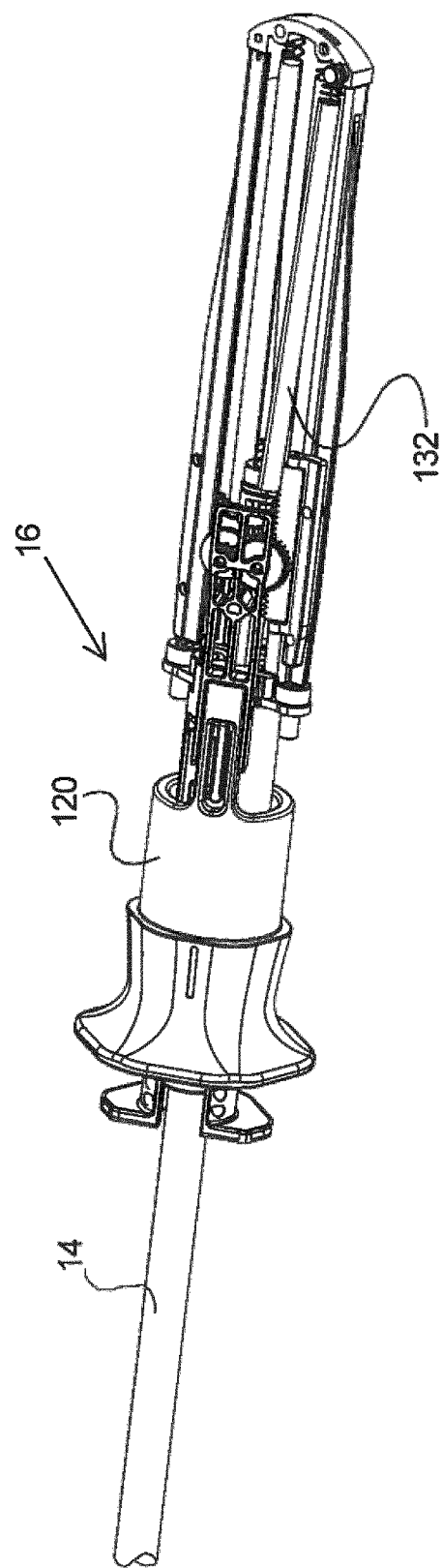
Figure 40:
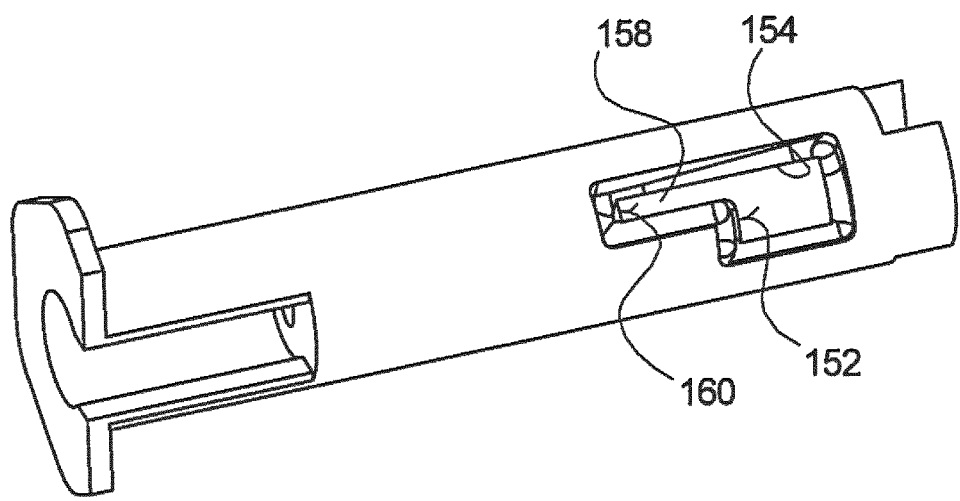
Figure 41:
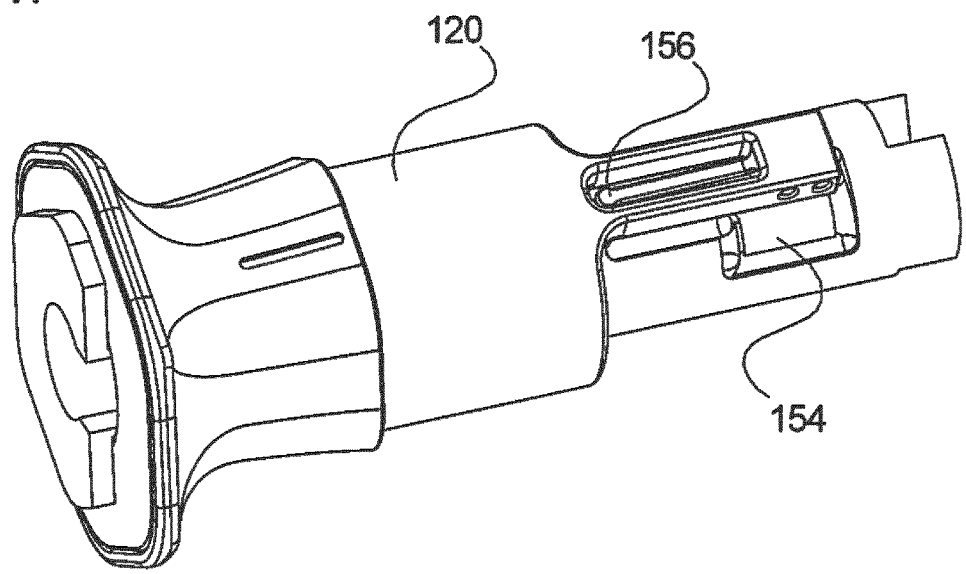

The figures illustrate an exemplary embodiment of the invention. The drawings show:

FIG. 1, a perspective view of an anchor arrangement according to the invention;

FIG. 2, a sectional view of an anchor arrangement in the set state on a tissue to be repaired;

FIG. 3, a sectional view of a hollow needle for setting the anchor arrangement;

FIG. 4, a perspective exploded view of an unfolding anchor of the anchor arrangement according to FIG. 1;

FIG. 5, a perspective view of the anchor according to FIG. 4 in a partially unfolded position;

FIG. 6, a view of an alternative embodiment of the unfolding anchor of the anchor arrangement, in a folded position;

FIG. 7, a view of the unfolding anchor according to FIG. 6 in a partially unfolded position;

FIG. 8, a view of the unfolding anchor according to FIG. 6 in an unfolded position and placed in the tissue;

FIG. 9, a view of a further alternative embodiment of the unfolding anchor with a concave contact surface;

FIG. 10, a view of a further alternative embodiment of the unfolding anchor with looped-through suture element in the folded position;

FIG. 11, a perspective view of the unfolding anchor according to FIG. 10 in the unfolded position;

FIG. 12, a perspective view of a further embodiment of the unfolding anchor comprising an end stop;

FIG. 13, a view of the unfolding anchor according to FIG. 12, shortly before reaching the unfolded position;

FIG. 14, a view of a single-piece embodiment of the folding anchor comprising a hinge;

FIG. 15, a view of the folding anchor according to FIG. 14 in an unfolded position and placed in the tissue;

FIG. 16, a view of a further alternative embodiment of the folding anchor with an alternative spring means, in the folded position;

FIG. 17, a view of the folding anchor according to FIG. 16 in a partially unfolded state;

FIG. 18, a view of a folding anchor in a folded position with a spreading means engaging therewith;

FIG. 19, a view of the folding anchor according to FIG. 18 in a partially unfolded position;

FIG. 20, a view of a folding anchor in a folded position with a spreading means engaging therewith, in an alternative embodiment;

FIG. 21, a view of the folding anchor according to FIG. 20 in a partially unfolded position;

FIG. 22, a perspective view of a needle tip of an alternative hollow needle comprising a longitudinal slot, and a distal end of an anchor arranged at the needle tip in a flush manner;

FIG. 23, a front view of the needle tip according to FIG. 22;

FIG. 24, a perspective view of a needle tip of an alternative embodiment of the hollow needle with a longitudinal slot;

FIG. 25, a perspective view of the hollow needle according to FIG. 24 with an anchor arrangement received thereon;

FIG. 26, a sectional view of the hollow needle according to FIG. 25;

FIG. 27, a perspective view of the hollow needle of a surgical instrument according to the invention, with a sliding element for tensioning the suture element;

FIG. 28, a view of a further alternative embodiment of the hollow needle with a proximal receiving region;

FIG. 29, a perspective view of an anchor arrangement and an alternative embodiment of an ejection device;

FIG. 30, a sectional view of an instrument handle with an anchor arrangement in the storage position;

FIG. 31, a sectional view of the instrument handle according to FIG. 37, with an anchor brought into a passive position;

FIG. 32, a perspective view of a further embodiment of a folding anchor in the folded position;

FIG. 33, a perspective view of the folding anchor according to FIG. 39, in the unfolded position;

FIG. 34, a perspective view of a manually actuated embodiment of the surgical instrument in the starting position;

FIG. 35, a view of the surgical instrument according to FIG. 34, in a setting-ready position;

FIG. 36, a view of the surgical instrument according to FIG. 34, in a set position;

FIG. 37, a view of the surgical instrument according to FIG. 34, on rotation into a release position;

FIG. 38, a perspective view of the surgical instrument according to FIG. 34, with the instrument handle removed;

FIG. 39, a perspective view of the surgical instrument according to FIG. 38, in the setting-ready position;

FIG. 40, a perspective view of a control cam of the instrument handle;

FIG. 41, a perspective view of the control cam according to FIG. 40, with actuation element arranged thereon;

FIG. 42, a perspective view of the surgical instrument according to FIG. 38, in the release position; and FIG. 43, a perspective view of the surgical instrument according to FIG. 38, in an ejected stop position.

FIG. 1 shows an anchor arrangement 2 for repair of a tissue G, which comprises at least one first anchor 4 and one second anchor 6, which are connected together by means of a suture element 8. The suture element 8 can for example consist of a thread, that is produced from an individual natural or synthetic fibre or a plurality of natural synthetic fibres.

As can be seen in particular from FIG. 2, the suture element 8 is fastened to the at least two anchors 4, 6 in such a way that a suture section 10 connecting the two anchors 4, 6, after setting of the anchor arrangement 2 on the tissue G to be repaired, such as a meniscus M having a tear R, can be shortened by applying tension Z to one end 12 of the suture element 8. For this purpose, a sliding knot K, for example, can be provided on the suture section 10. The tear R can be closed by shortening the suture section 10, as illustrated by the dot-dash line.

The suture element 8 and/or the anchor 4, 6 can be produced, at least partially, from an absorbable material. It is particularly advantageous if the absorbable material can be activated by means of a pulse, such as a heat or light pulse, or by application of a magnetic field. In this way, the anchor arrangement 2, can be at least partially gradually dismantled, in particular after a certain healing process of the tear R.

In order to be able to place the anchor arrangement 2 on the tissue G to be repaired, the at least two anchors 4, 6 are designed such that they can be received together with the suture element 8 on or in a hollow needle 14 of a surgical instrument 16, as illustrated in FIG. 3. They can then be pushed in said hollow needle toward a needle tip 18, in order that they can be set one after another at the desired position of the tissue G.

The two anchors 4, 6 each comprise a base body 20 that extends from a respective distal end 22 to a proximal end 24 and which thus forms a guide surface 26 on the outside thereof, which can at least partially be brought into contact with an inner side 28 of the hollow needle 14 in order to be guided in a positionally stable manner by same when sliding in the distal direction to the needle tip 18.

Thus, by means of the hollow needle 14, passages 30 can be pierced through the tissue G via which the anchors 4, 6 can be positioned one after another on a first side 32 of the tissue G, as illustrated in FIG. 2. After setting the first anchor 4, the suture element 8 extends through the corresponding passage 30 along a second side 34 of the tissue G and through the passage 30 to the second anchor 6. A recess is provided 36 on the second anchor, through which the suture element 8 is looped and extends back via the passage 30 to the end 12.

In order to ensure that the anchor 4, 6, after exit from the hollow needle 14 and application of the tensile force Z on the suture element 8, does not re-enter the respective passage 30, the anchors 4, 6 comprise deflecting means 38, via which a torque MD can be applied to at least parts of the anchors 4, 6 during ejection, i.e. in particular during or after the exit from the needle tip 18.

For this purpose, the at least two anchors 4, 6 are designed to be multi-piece, in particular two-piece, as can be seen in particular from FIG. 4. The deflecting means 38 are formed by a joint 54 and a spring means 68 which acts between a first anchor section 50 and a second anchor section 52. For this purpose, an elastically deformable spring arm 51, for example, is formed on the first anchor section 50, which acts on a stop cam 53 which is held in a position stable manner on the second anchor section 52. In a folded position of the anchor 4, 6 according to FIG. 3, the spring arm 51 presses against said stop cam 53 and this generates a torque between the two anchor sections 50, 52, by means of which these are pretensioned in an unfolded position. The stop cam 53 is thus formed, as shown by way of example in FIG. 4, on a locking section 55, which serves to secure both anchor sections 50, 52 in the assembled state and enables easier mounting of the respective anchors 4, 6 despite the small dimensions thereof.

In order to ensure a particularly secure mounting of the anchors 4, 6 on the first side 32 of the tissue G, these can be provided for example with a rough surface at least in a contact region 48, as shown in FIG. 2.

As can be seen from FIG. 5, after being set out of the hollow needle 14, these anchors 4, 6 are unfolded by the spring means 68 to such an extent that re-entry into the passage 30 is not possible. The two anchor sections 50, 52 have a rounding 58 at their respective free ends 56, by means of which they can be pressed against the tissue G by applying the tensile force Z to the suture element 8, in such a way that they can be moved further into the completely unfolded position. Alternatively, the spring means 68 can also be designed such that the generated torque MD is sufficient in order to bring the anchors 4, 6 completely into the unfolded position after exit from the hollow needle 14.

As shown by way of example in a further embodiment according to FIG. 6, the two anchor sections 50, 52 are initially arranged in a folded position, in which they can be received in the hollow needle 14 and moved along same. The two anchor sections 50, 52 can have a rounding 58 at a respective proximal free end 56, such that after setting, for example by pressing the free ends 56 against the encountered tissue G, in particular in addition to the spring means 68 provided according to the embodiment, they can be pivoted away from one another as illustrated in FIG. 7. Through further pulling on the suture element 8, the two anchor sections 50, 52 can be unfolded into the unfolded position according to FIG. 8, in which the anchors 4, 6 have a maximum extension, which prevents a re-entry into the respective passage 30. In addition, means can be provided on the anchors 4, 6, through which the anchor sections 50, 52 can be mutually locked in the unfolded position (not illustrated).

As illustrated in the embodiment according to FIG. 9, it is also possible to form the two anchor sections 50, 52 in such a way that in the unfolded position they form a common, concave contact surface 60 which matches a curve of a convex surface of the respective tissue G to be repaired, in order to guarantee a particularly secure attachment of the anchors 4, 6.

FIG. 10 shows a further embodiment of the anchors 4, 6 in the folded position, in which the suture element 8 is looped through an arrangement of receiving openings 62 of both anchor sections 50, 52, in such a way that the application of the tensile force Z on the suture element 8 brings about a shortening of the suture element 8 inside the anchors 4, 6. This shortening in turn results in oppositely directed torques MD being applied to the two anchor sections 50, 52 such that they are folded apart as illustrated in FIG. 11.

As can be seen from FIG. 12, stop surfaces 64 can be formed on both anchor sections 50, 52 which, during unfolding, move the respective anchors 4, 6 onto a corresponding respective stop surface 64 of the other anchor section 52, 50, as can be seen in FIG. 13. In the final unfolded position, these stop surfaces 64 then contact each other and thus form an end stop for the respective other anchor section 50, 52.

FIG. 14 shows a further embodiment of the anchors 4, 6, in which the two anchor sections 50, 52 are formed as one piece and can be pivoted with respect to one another by means of an integral hinge 66. In the illustrated folded position, the two anchor sections 50, 52 are folded together so as to be able to be received and moved inside the hollow needle 14, wherein the first anchor section 50 closes the needle tip 18 of the hollow needle 14. After setting of the anchors 4, 6 concerned, a deflection occurs into the unfolded position according to FIG. 15, in which both anchor sections 50, 52 are arranged in a line and thus have a maximum extension so that they can be brought into contact on the tissue G in a position stable manner.

In this case, the deflection movement can result for example through an elastic recovery force of the integral hinge 66. For this purpose, the integral hinge 66 must be formed from a correspondingly elastically deformable material and be moved under tension towards the unfolded position in the hollow needle 14.

Alternatively or in addition, it is also possible to produce at least parts of the anchor 4, 6, preferably the integral hinge 66, from a shape-memory material, which can be activated for example by exposure to light, temperature or an electric or magnetic field, in order, after setting of the folded position, to reform the anchor 4, 6 concerned back into the unfolded position.

Such a shape-memory material can be activated for example by a temperature in the range of a normal body temperature. The anchor 4, 6 in question is then deformed into the folded position and held at a lower temperature.

After setting, the anchor 4, 6 is then warmed by the ambient temperature in the body to an appropriate value and the shape-memory material is activated, resulting in a deflection of the anchor sections 50, 52 into the unfolded position. It is also conceivable that the anchor concerned comprises at least two activatable deformation sections, the shape-memory material of which is designed such that it is deflected over a period of time (not illustrated). In this way, for example, it can be ensured that, through the first deformation, directly after setting, the anchors 4, 6 concerned are unable to re-enter the passage 30, while by means of the second deformation a desired final shape of the anchor 4, 6 is produced, in which shape it then remains permanently in the body.

FIG. 16 shows a further embodiment of an anchor 4, 6 comprising at least two anchor sections 50, 52 which are movable relative to each other, with the spring means 68 arranged therebetween, by means of which the anchor sections 50, 52 that are received in the folded position in the hollow needle 14, can be pretensioned away from one another.

As can be seen from FIG. 17, after setting from the hollow needle 14, said anchor 4, 6 is unfolded by the spring means 68 to such an extent that a re-entry into the passage 30 is not possible. In this embodiment also, the two anchor sections 50, 52 have the rounding 58 at their respective free ends 56, through which they can be pressed against the tissue G by applying the tensile force Z to the suture element 8, in such a way that they can again be moved into the completely unfolded position.

In a further embodiment of the anchors 4, 6 according to FIG. 18, the anchor sections 50, 52 together form a common spreading receptacle 70 in the folded position, preferably in the state received in the hollow needle 14, at the proximal end 24 of the anchor 4, 6 concerned. Spreading means 72 of the ejection device 46 can be applied in this spreading receptacle 70, having for example a tapered region 76 at the distal end 74 thereof. The spreading means 72 serve to fold apart the two anchor sections 50, 52 through a wedge effect, after exit of the anchor 4, 6 from the hollow needle 14, as illustrated in FIG. 19. Such a spreading receptacle 70 can also be provided for each of the other embodiments of the anchors 4, 6.

FIG. 20 shows an alternative embodiment of the spreading means 72, in which at least two elastic, radially outward pretensioned spreading arms 78 are provided at the distal end 74. These elastic spreading arms 78 act on the spreading receptacle 70 of the anchor 4, 6 received in the hollow needle 14 in the folded position. After the exit of this anchor 4, 6, both anchor sections 50, 52 are folded apart from one another by the elastic restoring forces of the spreading arms 78, as illustrated in FIG. 21.

As can be seen from FIGS. 22 and 23, the hollow needle 14, by means of which the anchors 4, 6 are set, has a closed circumferential cross-section Q at least at the needle tip 18. The cross-section Q, as illustrated, is formed materially closed. In addition, the hollow needle 14 is form completely closed, wherein a longitudinal groove 90 is introduced on the outside 88 thereof, which during a setting procedure serves to at least partially receive the suture element 8.

As can further be seen from FIGS. 22 and 23, the cross-section Q of the hollow needle 14 deviates, at least towards the needle tip 18, from a circular profile. Moreover, the bottom 92 of the cross-section tapers in a heart shape. In addition, the edge 94 of the needle tip 18 slopes downwards with respect to the setting direction RS defined by the longitudinal extent of the hollow needle 14 to the needle tip 18, slanting to this bottom 92 of the cross-section. The tip edge 94 has a contact angle WS, which matches a contact angle WA formed by a chamfer 96 at the distal end 22 of the anchor 4, 6 with respect to the longitudinal axis of the base body 20. Through this and through a matched cross-section of the anchors 4, 6, the needle tip 18 can be closed in a substantially flush and sealed manner. In addition, the two anchors 4, 6 are guided by the corresponding heart-shaped profile of the guide surface 26 thereof, in a predetermined rotational position with respect to the hollow needle 14.

FIG. 24 shows an alternative embodiment of the hollow needle 14, in which the closed circumferential cross-section Q of the needle tip 18 has a splice 98 of two edges 102 of a longitudinal slot 100. The two edges 102 contact each other in the unloaded state, at least at the needle tip 18. During setting of the anchors 4, 6, the longitudinal slot 100 between the two edges 102 can be opened however, as illustrated in FIG. 25, by pressing in of a section of the suture element 8 or a protruding part of the anchor 4, 6 in question (not illustrated).

Alternatively, the free cross-section of the hollow needle 14 can be sized to be so narrow, at least in sections, that the hollow needle 14 spreads through the movement of the anchor 4, 6 alone in the distal direction and the splice 98 thus opens. In particular, this can prevent the suture element 8 from being damaged, or even cut, when passing the splice 98. In each case, a part of the anchor arrangement 2 projecting from the inside of the hollow needle 14 through the longitudinal slot 100, such as in particular the suture element 8 according to FIG. 26, is set out of the hollow needle 14 together with the second or further anchor 6.

Tensioning means can be provided on the hollow needle 14, in order to be able to prevent obstructions due to the suture element 8 during the setting procedure, by means of which the suture element 8 is tensioned and makes contact adjacent to the hollow needle 14. A sleeve-shaped sliding element 104 can be provided as the tensioning means, as illustrated in FIG. 27, which can be pushed along the hollow needle 14 and on which the suture element is deflected. In order to tension the suture element 8, a spring force F can act on the sliding element 104 in the proximal direction.

In order that the at least two anchors 4, 6 of the anchor arrangement 2 can be set in a non-specified period of time, one after another from the hollow needle 14, the ejection element 44 can be brought directly into contact with the anchor 4, 6 arranged in the setting-ready position, in order to be able to set same out of the needle tip 18. For this purpose, the hollow needle 14 comprises a receiving section 106, as illustrated in FIG. 28, which is proximal to a distal section 108. The receiving section 106 has a larger cross-section than the distal section 108, so that the ejection element 44 can be guided past the second anchor 6 that is received in the receiving section 106 and can be applied directly on the first anchor 4 in the setting-ready position.

As can further be seen from FIG. 28, the second anchor 6 received in the receiving section 106 is supported in the setting direction RS by a cross-section seam 110 of the hollow needle 14. In addition, a further support means 112 is provided, for example in the form of a movable slide, which supports the second anchor at the proximal end 24 thereof. Through this, the second anchor 6 is received in the passive position thereof in the receiving section 106, stably secured in both directions with respect to the hollow needle 14.

In order to set the first anchor 4, it is moved by means of the ejection element 44 in the setting direction RS, wherein the ejection element 44 moves past the second anchor 6 secured in the receiving section 106. After successful ejection of the first anchor 4, the ejection element 44 is then moved in the proximal direction to behind the second anchor 6. This enables a lateral avoidance of the second anchor 6 and passing by same of the cross-section seam 110 into the distal section 108, such as for example by means of a slightly resilient biasing of the proximal end 24 by the support means 112.

After this, the ejection element 44 can now be applied to the proximal end 24 in order to move the second anchor 6 along the distal section 108, until the second anchor 6 is arranged in the setting-ready position, in which it closes the needle tip 18.

Alternatively to the above-mentioned procedure, an ejection device 46 can be provided which comprises an individual ejection element 44 for each of the at least two anchors 4, 6 that are to be set. This principle is illustrated in FIG. 29 on the basis of two folding anchors 4, 6, for which the ejection elements 44 are provided with spreading means 72. The use of at least two separate ejection elements 44 is however also possible for each of the other above-described embodiments of the anchors 4, 6.

In addition, the hollow needle 14 can also be connected to a handle receptacle 114, as illustrated in FIG. 30, which is located in an instrument handle 116 of the surgical instrument 16. In said handle receptacle 114, which has a clearly larger free cross-section with respect to the distal section 108 (see FIG. 28) and also with respect to the proximal receiving section 106 of the hollow needle 14, at least one of the anchors 4, 6, or two or more anchors 4, 6, can be received, before being moved, in order to prepare a setting procedure, into the passive position or into the setting-ready position inside the hollow needle 14.

As can be seen from FIG. 30, the anchors 4, 6 received in the handle receptacle 114 can thus be received in a tension-free position, such as a partially unfolded position for example. In this way, elastic spring means 68 of unfolding anchors 4, 6 in particular can be relieved during storage in the handle receptacle 114, in order to allow a reduction in the elastic restoring force generated by the spring means 68 to be avoided.

The anchors 4, 6 can be moved out of the handle receptacle 114 into the distal section 108 in order to prepare a setting procedure or, if provided, also into the proximal receiving section 106 of the hollow needle 14, as illustrated in FIG. 31. To this end, the ejection device 46 comprises for example a slide 118 that can be operated by the user, by means of which the anchor 4, 6 concerned can be moved into the desired position, or alternatively into the setting-ready position in the hollow needle 14. In the illustrated embodiment of the first anchor 4 as a folding anchor, this is simultaneously brought into the folded position. The slide 118 can be operated for example via an operating element 122, that is itself movably mounted on the rest of the instrument handle 116. Thus the operating element 122 can be moved in the distal direction to a position illustrated by the dot dash line, which corresponds to the setting-ready position of the anchor 4, 6 concerned.

Depending on the embodiment of the ejection device 46, the slide 118 can itself function as an ejection element 46 or, as shown, be separately formed as a separate ejection element 46. In both cases, ejection can thus result from movement of an operating element 120, which is illustrated by way of example as a sliding sleeve.

It should also be noted that alternatively to the various embodiments of the unfolding anchors 4, 6, illustrated by way of example, which each provide a horizontal folding movement when the needle tips 18 arranged below, depending on the application, the folding anchors 4, 6 can also be folded into any other angular position with respect to a setting axis AS defined by the distal section 108 of the hollow needle 14. FIGS. 32 and 33 show an exemplary embodiment of a folding anchor 4, 6, which provides a vertical unfolding of the two anchor sections 50, 52 when the needle tips 18 are arranged below.

It is also noted that the hollow needle 14 can also be curved at the distal end 12 thereof, depending on the intended application, as illustrated by the dot-dash line in FIG. 28.

As already described above, the surgical instrument 16 can for example be designed as a manually operated device. In this case the surgical instrument 16 comprises the actuating element 120, which is arranged adjacent to the instrument handle 116 in a starting position that can be seen in FIG. 34 and can be moved with respect thereto, parallel to the setting direction RS.

In order to move one of the anchors 4, 6 into the setting-ready position at the needle tip 18, the actuating element 120 is brought into the position illustrated in FIG. 35, in which it is spaced apart from the remainder of the instrument handle 116.

In order to set the anchor 4, 6 concerned, the actuating element 120 must then be rotated about the axis of same as illustrated in FIG. 36. Only after attaining the specified rotation position can the actuating element 120 according to FIG. 37 be moved further in the setting direction RS, in order to eject the anchor 4, 6 concerned. After this setting procedure, a manual or automatic return movement of the actuating element 120 takes place, returning to the starting position illustrated in FIG. 34.

As can be seen in FIG. 38, the surgical instrument 16 comprises a toothed gearing 124, that is used to control the movement sequence of the ejection means 46. The toothed gearing 124 comprises a multi-stage cog 126 held on the actuating element 120, which meshes with both the gearing 128 fixed in the housing of the instrument handle 116, as well as with the cog 130 that is coupled to the ejection device 46, for example by means of a belt drive (not illustrated). This allows the relative movement of the actuating element 120 with respect to the instrument handle 116 to be transferred with a specified ratio onto the ejection device 46, in order for example to produce, by means of a relatively small movement of the actuating element 120, relatively large movements of the ejection device 46 or of at least one ejection element 44 or of at least one slide 118. This makes it possible, in particular, to bring the respective anchor 4, 6 from the passive position thereof in the proximal receiving section 106, by means of a small relative movement of the actuating element 120 with respect to the instrument handle 116, into the setting-ready position in the hollow needle 14, the position illustrated in FIG. 39.

In addition it is also possible, to design the toothed gearing 124 such that one of a plurality of ratios can be set (not illustrated).

In the position of the actuating element 120 or of the ejection device 46 corresponding to the setting-ready position of the anchor 4, 6 concerned, according to FIGS. 35 and 39, the actuation element 120 comes to into contact with an end stop 152 in the setting direction RS. As can be seen in particular from FIGS. 40 and 41, said end stop 152 is formed by a control cam 154 provided on the instrument handle 116, into which a cam 156 protrudes, which is carried along by the actuating element 120.

From this end stop position, the cam 156 can be brought by the rotary action of the actuating element 120 illustrated in FIG. 36 into a release position illustrated in FIG. 42, in which it is arranged laterally separated from the end stop 152 with respect to the setting direction RS. At the same time, in the release position, the meshed engagement of the cogs 126 with the gearing 128 fixed to the housing is released.

The actuating element 120 can move with the cam 156, thus from the release position along a longitudinal section 158 (see FIG. 40) of the control cam 154, wherein the ejection device 46 moves further in the setting direction RS, in order to eject the anchor 4, 6 concerned. Due to the separation of the cogs 126 from the gearing 128 fixed to the housing, there is no ratio by which the user can very directly control the setting procedure.

After setting of the anchor 4, 6 concerned, the cam 156 comes into the position illustrated in FIG. 43, in contact with an ejection stop 160 of the control cam 154 (see FIG. 40). In this position, a further movement of the actuating element 120 and the ejection device 46 is blocked in the setting direction RS, in order for example to prevent an exit, or too far an exit, of the ejection element 44 at the needle tip 18.

From this ejection end stop position, the actuating element 120 can be moved back with the ejection device 46, for example after actuation of a release button (not illustrated) by means of the spring force of a return spring means 132, into the starting position according to FIG. 41. In this way, for example, the ejection element 44 of the ejection device 46 can be positioned as described above at the proximal end 24 of the second anchor 6 which is subsequently to be set. Then, the actuating element 120 can be moved again into the position according to FIG. 38, in order to now bring the second anchor 6 into the setting-ready position at the needle tip 18.

An acoustic, optical or tactile-perceptible signal transmitter (not illustrated) can be provided for example, which is automatically activated as soon as the second or further anchor 6 concerned is in the setting-ready position. The ejection device 46 can also be designed such that it is a locked in the setting-ready position of one of the anchors 4, 6, for example by means of the toothed gearing 124, against a movement counter to the setting direction RS, so that the ejection element 44 supports the anchor 46 concerned in the proximal direction.

The invention claimed is:

1. An anchor arrangement for surgical tissue repair, comprising:
   a first anchor and a second anchor, movable along a hollow needle for placement on a tissue to be repaired, and connected to each other via a suture element, the suture element being a flexible thread connected to one of the first anchor and second anchor at a location spaced from a longitudinal axis of the hollow needle while the first anchor and second anchor are in the hollow needle,
   wherein the first anchor and the second anchor each extend between a distal end and a proximal end and form a guide surface on an outside thereof for contacting an inside of the hollow needle at least in part,
   wherein deflectors are provided on the anchors, via which a torque can be applied at least in part to the first and second anchors during or after setting, and
   wherein at least one of the first and second anchors has at least two anchor sections, which are movable relative to each other and which can be pivoted relative to each other between a folded position, in which the guide surface spans a cross-section perpendicular to the longitudinal axis of the hollow needle deviating from a circular profile, and an unfolded position, and the at least two anchor sections are connected together via a joint.

2. The anchor arrangement according to claim 1, wherein the guide surface, in the folded position of the at least two anchor sections which are movable relative to each other, is heart-shaped, oval or egg-shaped in the sense of a circumferentially convex profile.

3. The anchor arrangement according to claim 2, wherein the at least two anchor sections are pretensioned in the direction of the unfolded position, wherein the suture element is deflected on the at least two anchor sections in such a way that an unfolding torque can be applied thereto.

4. The anchor arrangement according to claim 1, wherein each of the at least two anchor sections are supported by an end stop of the other anchor section of the at least two anchor sections in the unfolded position.

5. The anchor arrangement according to claim 1, wherein in the folded position, the at least two anchor sections form a common spreading receptacle at the proximal end of at least one anchor, which can be spread by applying a spreader.

6. A surgical instrument for setting an anchor arrangement for surgical tissue repair, comprising:
a hollow needle, which forms a needle tip at a distal end thereof;
a first anchor and a second anchor, movable along the hollow needle for placement on a tissue to be repaired, and connected to each other via a suture element, said first anchor and the second anchor each extending between a distal end and a proximal end and forming a guide surface on an outside thereof for contacting an inside of the hollow needle at least in part;
deflectors on the first and second anchors, via which a torque can be applied at least in part to the first and second anchors during or after setting, wherein at least one of the first and second anchors has at least two anchor sections, which are movable relative to each other and which can be pivoted relative to each other between a folded position, in which the guide surface spans a cross-section deviating from a circular profile, and an unfolded position, said at least two anchor sections being connected together via a joint; and
an ejection device comprising an ejection element slidably mounted inside the hollow needle, wherein said ejection element has a first portion contacting the first anchor for selectively, manually moving the first anchor along the hollow needle and a second portion contacting the second anchor for selectively, manually moving the second anchor along the hollow needle,
wherein the hollow needle has a closed circumferential or closable cross-section at the needle tip and has a cross-section deviating from a circular profile at least towards the needle tip.

7. The surgical instrument according to claim 6, wherein the hollow needle has a longitudinal slot, and two opposite edges of the longitudinal slot come together at the needle tip in an unloaded condition.

8. The surgical instrument according to claim 7, wherein the two opposite edges can be expanded by pressing in a section of the needle tip or the first or second anchor.

9. The surgical instrument according to claim 6, wherein the needle tip can be closed in a flush manner by the first and second anchors of the anchor arrangement received therein.

10. The surgical instrument according to claim 6, wherein tensioners are provided on the hollow needle for tensioning the suture element, which comprises a sliding element that can be slid along the hollow needle, on which the suture element is deflected and that is pretensioned in a proximal direction.

11. The surgical instrument according to claim 6, wherein at the needle tip, the hollow needle comprises a distal section and a receiving section arranged proximal thereto which has an extended cross-section with respect to the distal section.

12. The surgical instrument according to claim 11, wherein in the extended cross-section, the ejection element can be guided past the second anchor.

13. The surgical instrument according to claim 11, wherein a support is provided in the proximal receiving section, wherein the second anchor can be supported in an axial direction.

14. The surgical instrument according to claim 6, wherein a toothed gearing is provided for controlling movement sequences of the ejection device and the toothed gearing has a predetermined ratio between a movable actuation element and the ejection element.

15. The surgical instrument according to claim 14, wherein the anchors can be supported in a setting-ready position in a proximal direction by the ejection device, and the movement thereof in the proximal direction is thus locked.

16. The surgical instrument according to claim 14, wherein the actuation element can be applied on an end stop and the ejection device is thus arranged in an end stop position, which corresponds to a setting-ready position of the respective accompanying anchor.

17. The surgical instrument according to claim 16, wherein the actuation element can be rotated into a release position on separation of the toothed gearing from the end stop position, in which the actuation element can again be moved in a setting direction.

18. The surgical instrument according to claim 16, wherein the end stop position and a release position are provided by a control cam, into which a cam connected to the actuation element protrudes.

19. The surgical instrument according to claim 14, wherein an ejection stop is provided, wherein the movement of the ejection device can be limited in a distal direction, and the ejection device is movable by a return spring from an ejection end stop position into a starting position, wherein the ejection device can be simultaneously positioned behind an anchor received in a receiving section.

* * * * *